(12) United States Patent
Durr et al.

(10) Patent No.: US 12,376,744 B2
(45) Date of Patent: Aug. 5, 2025

(54) COMPUTATIONAL LIGHTFIELD OPHTHALMOSCOPE

(71) Applicant: THE JOHNS HOPKINS UNIVERSITY, Baltimore, MD (US)

(72) Inventors: Nicholas J. Durr, Baltimore, MD (US); Faisal Mahmood, Baltimore, MD (US); Gregory Mckay, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 761 days.

(21) Appl. No.: 16/972,483

(22) PCT Filed: Jul. 2, 2019

(86) PCT No.: PCT/US2019/040393
§ 371 (c)(1),
(2) Date: Dec. 4, 2020

(87) PCT Pub. No.: WO2020/010138
PCT Pub. Date: Jan. 9, 2020

(65) Prior Publication Data
US 2021/0267451 A1    Sep. 2, 2021

Related U.S. Application Data

(60) Provisional application No. 62/694,623, filed on Jul. 6, 2018.

(51) Int. Cl.
*A61B 3/12* (2006.01)
*A61B 3/117* (2006.01)
(Continued)

(52) U.S. Cl.
CPC ............ *A61B 3/12* (2013.01); *A61B 3/117* (2013.01); *A61B 3/14* (2013.01); *A61B 5/6898* (2013.01); *G02B 27/48* (2013.01)

(58) Field of Classification Search
CPC ......... G02B 27/48; A61B 5/6898; A61B 3/14; A61B 3/117; A61B 3/12
(Continued)

(56) References Cited

U.S. PATENT DOCUMENTS 6,271,915 B1 * 8/2001 Frey .................. A61F 9/00806
356/124
2013/0208244 A1 * 8/2013 Sakagawa ............ A61B 3/103
351/205

(Continued)

FOREIGN PATENT DOCUMENTS

JP       2017108995 A      6/2017
WO    WO-2011029064 A1 *  3/2011 .............. A61B 3/12
(Continued)

OTHER PUBLICATIONS

Extended European Search Report in European Application No. 19830933.8 mailed on Feb. 18, 2022, 6 pages.
(Continued)

*Primary Examiner* — Mustak Choudhury
(74) *Attorney, Agent, or Firm* — MH2 Technology Law Group LLP

(57) ABSTRACT

A device for ocular diagnostics may include one or more light sources configured to illuminate an anterior segment of a patient's eye, a diffuser positioned to receive light remitted from the anterior segment of the patient's eye, and configured to provide a pattern based on the light remitted, and an image sensor configured to obtain one or more images of the pattern to enable determination of one or more properties of the patient's eye.

31 Claims, 15 Drawing Sheets

(51) Int. Cl.
  *A61B 3/14* (2006.01)
  *A61B 5/00* (2006.01)
  *G02B 27/48* (2006.01)
(58) Field of Classification Search
  USPC .......................................... 351/205–206, 246
  See application file for complete search history.

(56) References Cited

U.S. PATENT DOCUMENTS

| | | |
|---|---|---|
| 2015/0260978 A1 | 9/2015 | Cremer et al. |
| 2015/0289760 A1* | 10/2015 | Zhou .................. G01J 9/00 351/205 |
| 2016/0128566 A1* | 5/2016 | Durr .................. A61B 3/1015 351/246 |
| 2016/0296112 A1 | 10/2016 | Fletcher et al. |
| 2017/0007121 A1* | 1/2017 | Gruppetta ............. A61B 3/102 |
| 2017/0086667 A1 | 3/2017 | Zhou et al. |
| 2017/0273558 A1* | 9/2017 | Tamura ................. G16H 30/20 |

FOREIGN PATENT DOCUMENTS

| | | | |
|---|---|---|---|
| WO | 2017052902 A1 | 3/2017 | |
| WO | 2017218539 A1 | 12/2017 | |
| WO | WO-2018013923 A1 * | 1/2018 | ............. A61B 3/028 |
| WO | WO-2020010138 A1 * | 1/2020 | ........... A61B 3/0025 |

OTHER PUBLICATIONS

International Search Report and Written Opinion in corresponding International Application No. PCT/US2019/040393 mailed on Oct. 30, 2019, 7 pages.

* cited by examiner

COMPUTATIONAL LIGHTFIELD OPHTHALMOSCOPE

CROSS-REFERENCE TO RELATED APPLICATIONS

This application is a national stage entry from International Application No. PCT/US2020/040393, filed on Jul. 2, 2019, and published as International Publication No. WO 2020/010138 A1 on Jan. 6, 2020, and claims priority under 35 U.S.C. § 119 to U.S. Provisional Patent Application No. 62/694,623, filed on Jul. 6, 2018 and entitled "COMPUTATIONAL LIGHTFIELD OPHTHALMOSCOPE," the contents of all which are incorporated by reference herein in their entirety.

GOVERNMENT RIGHTS

This invention was made with government support under contract number EB024700 awarded by the National Institutes of Health. The government has certain rights in the invention.

BACKGROUND

Over a billion people worldwide suffer from poor vision. Uncorrected refractive errors lead to lost productivity, limited access to education, and reduced quality of life. Uncorrected refractive errors can be corrected with a pair of prescription eyeglasses, which makes vision correction a cost-effective healthcare intervention, since prescription eyeglasses are fairly inexpensive. To prescribe eyeglasses, an eye examination is required, where the refractive errors of the eye are measured, and common diseases are screened for by imaging the posterior and anterior segment of the eye.

SUMMARY

According to some possible implementations, a device for ocular diagnostics may include one or more light sources configured to illuminate an anterior segment of a patient's eye, a diffuser positioned to receive light remitted from the anterior segment of the patient's eye, and configured to provide a pattern based on the light remitted, and an image sensor configured to obtain one or more images of the pattern to enable determination of one or more properties of the patient's eye.

According to some possible implementations, a computational lightfield ophthalmoscope device may include a first light source configured to emit light in a first wavelength range, a second light source configured to emit light in a second wavelength range, a third light source configured to emit light in a third wavelength range, a first beam splitter arranged to project light, emitted from the first light source, onto an anterior segment of a patient's eye, a second beam splitter arranged to project light, emitted from the second light source, onto a posterior segment of the patient's eye, a third beam splitter arranged to focus light, emitted from the third light source, onto a point in the posterior segment of the patient's eye, a fourth beam splitter arranged to reflect light remitted from the patient's eye, a diffuser positioned to receive light reflected by the fourth beam splitter, and configured to provide a pattern based on the light reflected by the fourth beam splitter, and an image sensor configured to obtain one or more images of the pattern for simultaneous, or near simultaneous, determination of aberrations of the patient's eye and derivation of a high-resolution image of the anterior segment of the patient's eye and a high-resolution aberration-corrected image of the posterior segment of the patient's eye.

According to some possible implementations, a computational lightfield ophthalmoscope device may include a first light source configured to periodically emit light at a first frequency, a second light source configured to periodically emit light at a second frequency, a third light source configured to periodically emit light at a third frequency, a first beam splitter arranged to project light, emitted from the first light source, onto an anterior segment of a patient's eye, a second beam splitter arranged to project light, emitted from the second light source, onto a posterior segment of the patient's eye, a third beam splitter arranged to focus light, emitted from the third light source, onto a point in the posterior segment of the patient's eye, a fourth beam splitter arranged to reflect light remitted from the patient's eye, a diffuser positioned to receive light reflected by the fourth beam splitter, and configured to provide a pattern based on the light reflected by the fourth beam splitter, and a camera configured to obtain one or more plenoptic images based on the pattern for simultaneous, or near simultaneous, determination of aberrations of the patient's eye and derivation of high-resolution images of the anterior segment of the patient's eye and the posterior segment of the patient's eye.

According to some possible implementations, a method may include emitting, by a first light source of a lightfield ophthalmoscope device, light in a first wavelength range, emitting, by a second light source of the lightfield ophthalmoscope device, light in a second wavelength range, emitting, by a third light source of the lightfield ophthalmoscope device, light in a third wavelength range, projecting, by a first beam splitter of the lightfield ophthalmoscope device, the light, emitted from the first light source, onto a cornea of a patient's eye, projecting, by a second beam splitter of the lightfield ophthalmoscope device, the light, emitted from the second light source, onto a retina of the patient's eye, focusing, by a third beam splitter of the lightfield ophthalmoscope device, light, emitted from the third light source, onto a point in the retina, reflecting, by a fourth beam splitter of the lightfield ophthalmoscope device, light remitted from the patient's eye, providing, by a diffuser of the lightfield ophthalmoscope device, a pattern based on light reflected by the fourth beam splitter, and obtaining, by a lens-less camera of the lightfield ophthalmoscope device, one or more images of the pattern for synergistic determination of aberrations of the patient's eye and derivation of a high-resolution image of the cornea and/or a high-resolution aberration-corrected image of the retina.

DETAILED DESCRIPTION

Figure 1A:
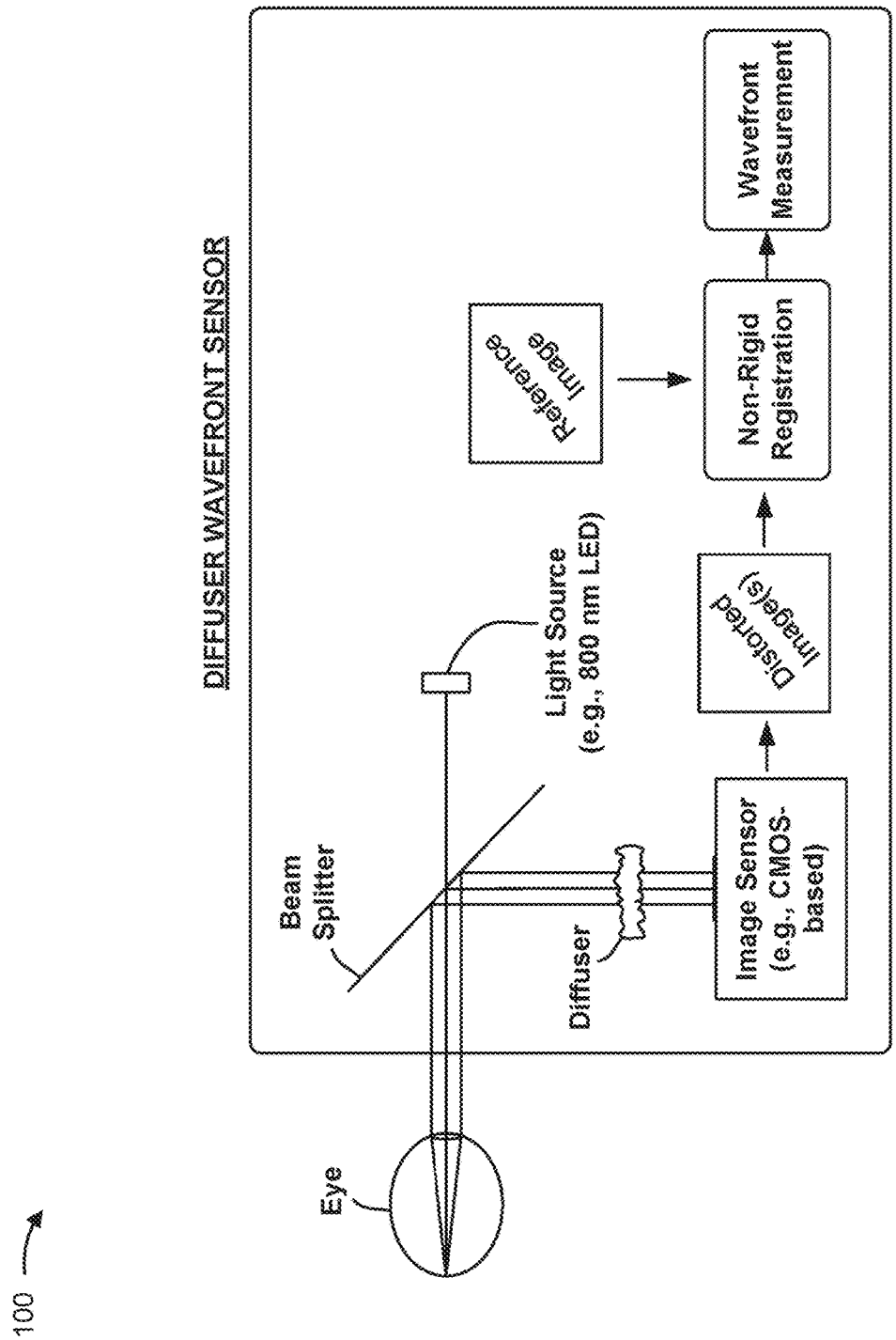
FIGS. 1A-1L are diagrams of an example implementation described herein.

The following detailed description of example implementations refers to the accompanying drawings. The same reference numbers in different drawings may identify the same or similar elements.

Obtaining an eyeglass prescription typically involves a comprehensive eye exam that screens for a variety of ocular diseases. Although people in many areas of the world are able to afford such an eye exam, there is a limited number of eye care professionals that can meet this demand. For example, in the United States, there is one eye care provider for about every 5,000 to 6,000 people, whereas in parts of Africa, there is only about one eye care provider for every one million people. A comprehensive eye exam generally includes refraction, tonometry, and slit-lamp and/or ophthalmoscope examinations of anterior and posterior segments of a patient's eye. A refraction examination determines an eyeglass prescription for correcting nearsightedness, farsightedness, astigmatism, and presbyopia. A tonometry examination measures intraocular pressure to screen for glaucoma. A slit lamp examination involves acquiring images of the anterior and posterior segments of an eye to screen for abnormalities, such as cataracts, macular degeneration, retinopathy, and vascular diseases. These examinations require the use of sophisticated, expensive equipment and extensive training to acquire and interpret measurements.

Some implementations, described herein, provide a computational lightfield ophthalmoscope device that is capable of utilizing computational optics to simultaneously (or near simultaneously, e.g., within less than 1 minute, 1 second, 0.1 seconds, and/or the like) characterize aberrations of a patient's eye and capture images of anterior and posterior segments of the patient's eye (e.g., including reconstructing a digitally-refocused, high-quality image of the fundus). In some implementations, characterizations of the aberrations of a patient's eye may be synergistic with imaging of the posterior segment of the patient's eye. In some implementations, an aberration profile, and images of the anterior and/or posterior segments of the eye, may be simultaneously (or near simultaneously) provided using a thin diffuser and a single plenoptic camera (e.g., a single lens-less camera). In some implementations, registration algorithm(s) and reconstruction algorithm(s), or an artificial neural network, are provided for determining the aberration profile and deriving high-resolution image reconstructions of the anterior and/or posterior segments of the eye, respectively. In some implementations, information based on the aberration profile and/or the caustic or speckle pattern, or the high-resolution image reconstructions, may be interpreted by a neural network (e.g., deep learning or deep learning with adversarial training) to automatically detect, localize, segment, and/or classify ocular pathologies (e.g., without a need for a highly-trained eye care provider).

In this way, several objective measurements of a comprehensive ocular exam may be provided using a single device or system. Employing a single computational lightfield ophthalmoscope device, such as that described herein, is advantageous over existing ocular examination instrumentation, since a single device can be used for refraction examination and imaging of anterior and posterior segments of a patient's eye. This reduces or eliminates a need to utilize three prior, complex systems (i.e., an autorefractor, a traditional ophthalmoscope, and a slit lamp) to conduct an eye exam, which simplifies, and reduces the costs of, such exams, thereby making affordable eye care accessible to more people. Additionally, a device that includes a minimal quantity of components—e.g., a light source (e.g., a light-emitting diode), a diffuser, and an image sensor, as described herein—and that provides objective measurements, reduces or eliminates a need for trained eye care providers to conduct eye exams, which also reduces the costs, and improves the overall accuracy, of such exams, thereby yielding more precise eyeglass prescriptions. Furthermore, utilizing a device, as described herein, provides synergistic measurements—e.g., wavefront information may be used to reconstruct higher quality retinal images, and such retinal images may be used to inform aberration measurements. This reduces or eliminates a need to utilize expensive closed-loop adaptive optics systems that may otherwise be needed to obtain high-resolution retinal images. High-resolution images of the fundus, provided by implementations described herein, also enable applications beyond eye examinations, including the assessment of various conditions relating to the brain (e.g., stroke severity, brain injury, neurodegenerative diseases, and/or the like), given that the retina may be a non-invasive portal to the brain. Such images of the fundus may also enable the assessment of a variety of health metrics, including, for example, blood pressure, cardiovascular risk factors, age, and/or the like. Furthermore, devices, described herein, may be implemented with no moving parts, and lightfield images of the posterior and anterior segments of the eye may be digitally-focused or digitally-refocused after the data is acquired. This simplifies the data acquisition process, as the user may not need to adjust the focus of the camera to acquire a sharp image.

FIGS. 1A-1L are diagrams of an example implementation 100 described herein. FIG. 1A is a schematic diagram of an example diffuser wavefront sensor. The diffuser wavefront sensor may, for example, be included in various implementations of the computational lightfield ophthalmoscope device described herein.

Figure 1B:
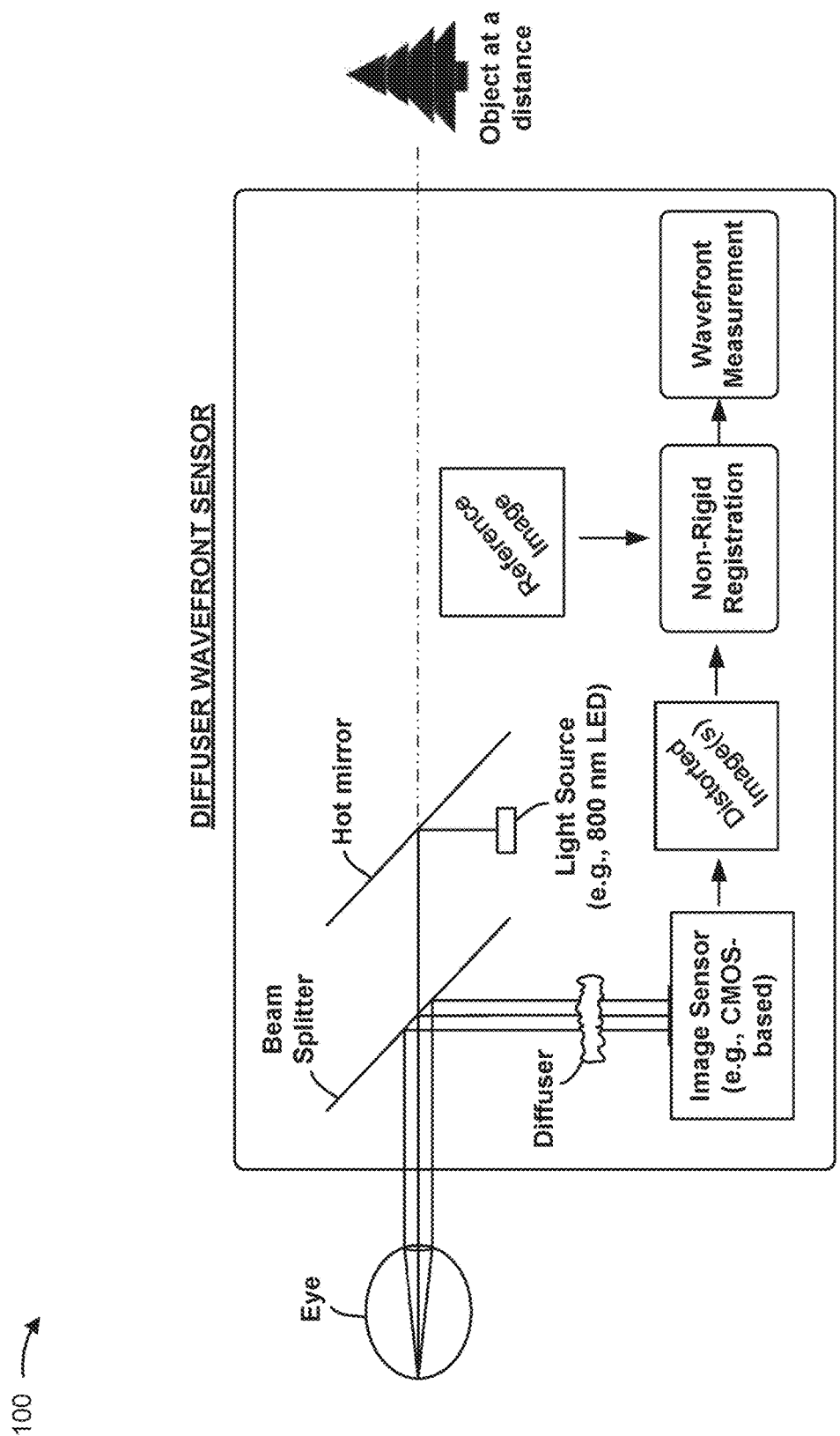

As shown in FIG. 1A, the diffuser wavefront sensor may include a light source, such as a light-emitting diode (LED) (e.g., an 800 nanometer (nm) LED and/or the like), a beam splitter, a diffuser, and an image sensor (e.g., a complementary metal-oxide-semiconductor (CMOS)-based sensor and/or the like). In some implementations, the diffuser and the image sensor, in conjunction with various functionalities, including an artificial neural network, a non-rigid registration algorithm, and/or a wavefront measurement function, may be utilized to obtain measurements of aberrations of a patient's eye. In some implementations, the diffuser wavefront sensor may include a hot mirror positioned to redirect light, emitted from the LED, towards the patient's eye (FIG. 1B). In such cases, and as shown in FIG. 1B, for example, the diffuser wavefront sensor may be implemented as a scope-like (e.g., open-view) device that permits a patient to view through the device (e.g., through the beam splitter and/or the like) into the environment. This permits a patient to focus the patient's view, through the device, on a static or mobile object (e.g., a tree, picture, and/or the like), which enables varied and flexible measurements to be made during examination.

In some implementations, the image sensor may be a camera phone, or a camera capable of providing images (e.g., wirelessly) to a mobile phone for processing and analysis. In such cases, the camera phone, or the camera, may include additional focusing optics.

In some implementations, the diffuser may be composed of one or more materials capable of randomly focusing light to provide a pattern (e.g., a caustic pattern and/or a speckle pattern). For example, the material(s) may include glass (e.g., simple ground glass), plastic, and/or the like having a surface with a randomized structure—e.g., randomly-arranged light refracting elements-configured to refract and/or reflect light such that a sharp, unique caustic or speckle pattern is produced (e.g., at a multiple of (e.g., about 5 times)

a roughness of the surface). In some implementations, both the top and bottom surface of the diffuser may have a roughened structure. In some implementations, the diffuser may be engineered to include such randomly-arranged light refracting elements. In some implementations, the diffuser may be designed to have a reproducible surface shape that produces a deterministic caustic or speckle pattern.

As shown in FIG. 1A, a patient's eye may be positioned such that light, from the light source, passes through the beam splitter, directly into the patient's eye (alternatively, in a case where a hot mirror is included, as shown in FIG. 1B, light, from the light source, may reflect off of the hot mirror, and pass through the beam splitter, toward the patient's eye). Light may be remitted from the patient's eye, and directed, by the beam splitter, towards the diffuser, which may produce a caustic or speckle pattern. The image sensor may detect the caustic or speckle pattern, and derive distorted image(s) of the caustic or speckle pattern (e.g., five-dimensional (5D) images and/or the like). As shown in FIG. 1A (and similarly in FIG. 1B), a reference image, and the distorted image(s), may be provided to the non-rigid registration algorithm for image registration, after which wavefront measurements may be made via the waveform measurement function to determine refractive errors of the patient's eye. In some implementations, the distorted image(s) of the caustic or speckle pattern may be processed by an artificial neural network to determine refractive errors of the patient's eye.

Figure 1C:
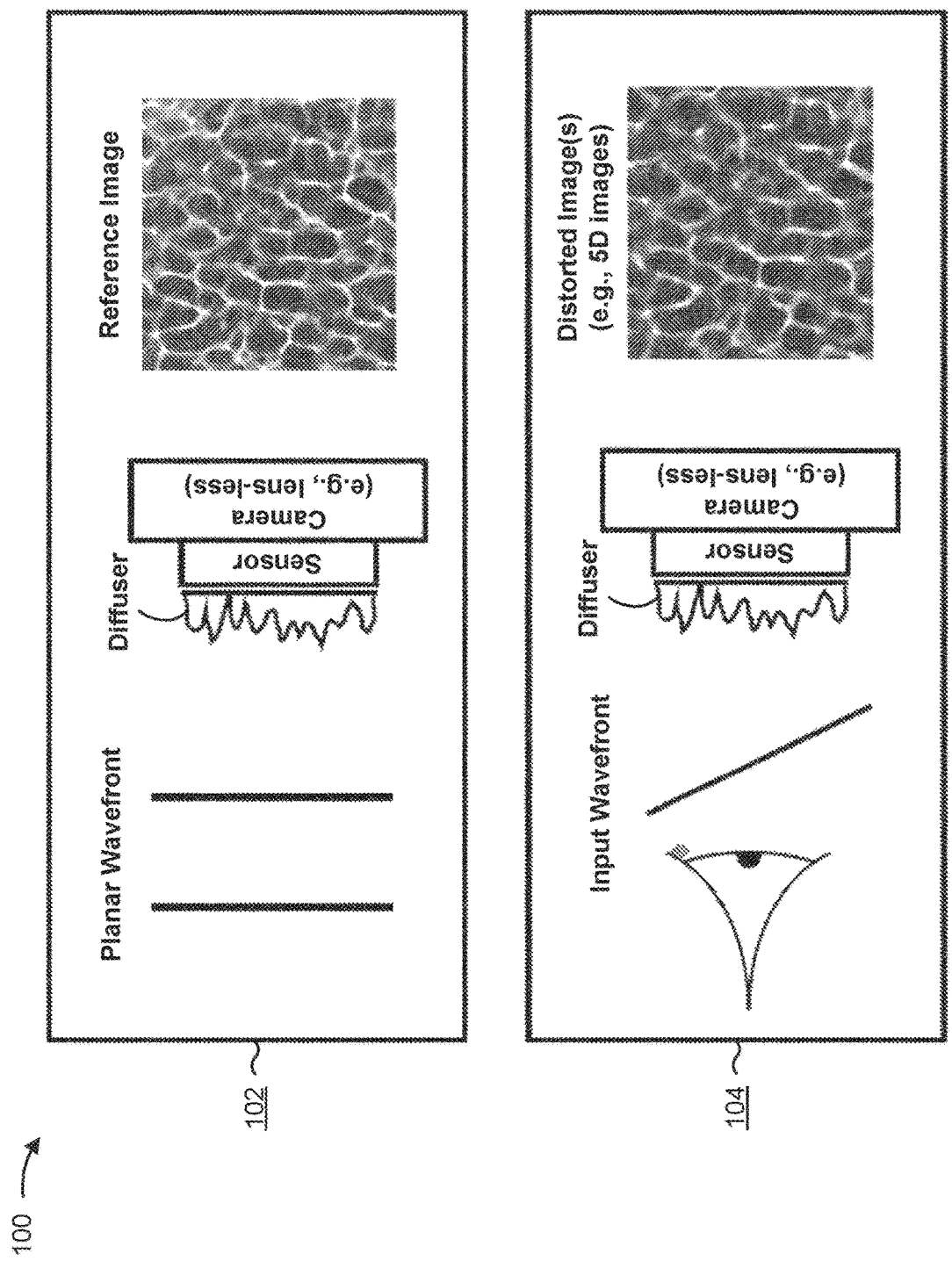

In various embodiments, the diffuser wavefront sensor may be utilized to derive the reference image. For example, as shown in FIG. 1C, a diffuser and a sensor and camera configuration (e.g., corresponding to the diffuser and the image sensor of the diffuser wavefront sensor shown in FIGS. 1A and/or 1B) may be used to derive a reference image based on a planar wavefront of light (reference number 102), and to derive the distorted image(s) based on input wavefront(s) of light remitted from a patient's eye (reference number 104). Distortions in images of caustic or speckle patterns, relative to the reference image, may be used to map aberrations of the patient's eye.

Figure 1D:
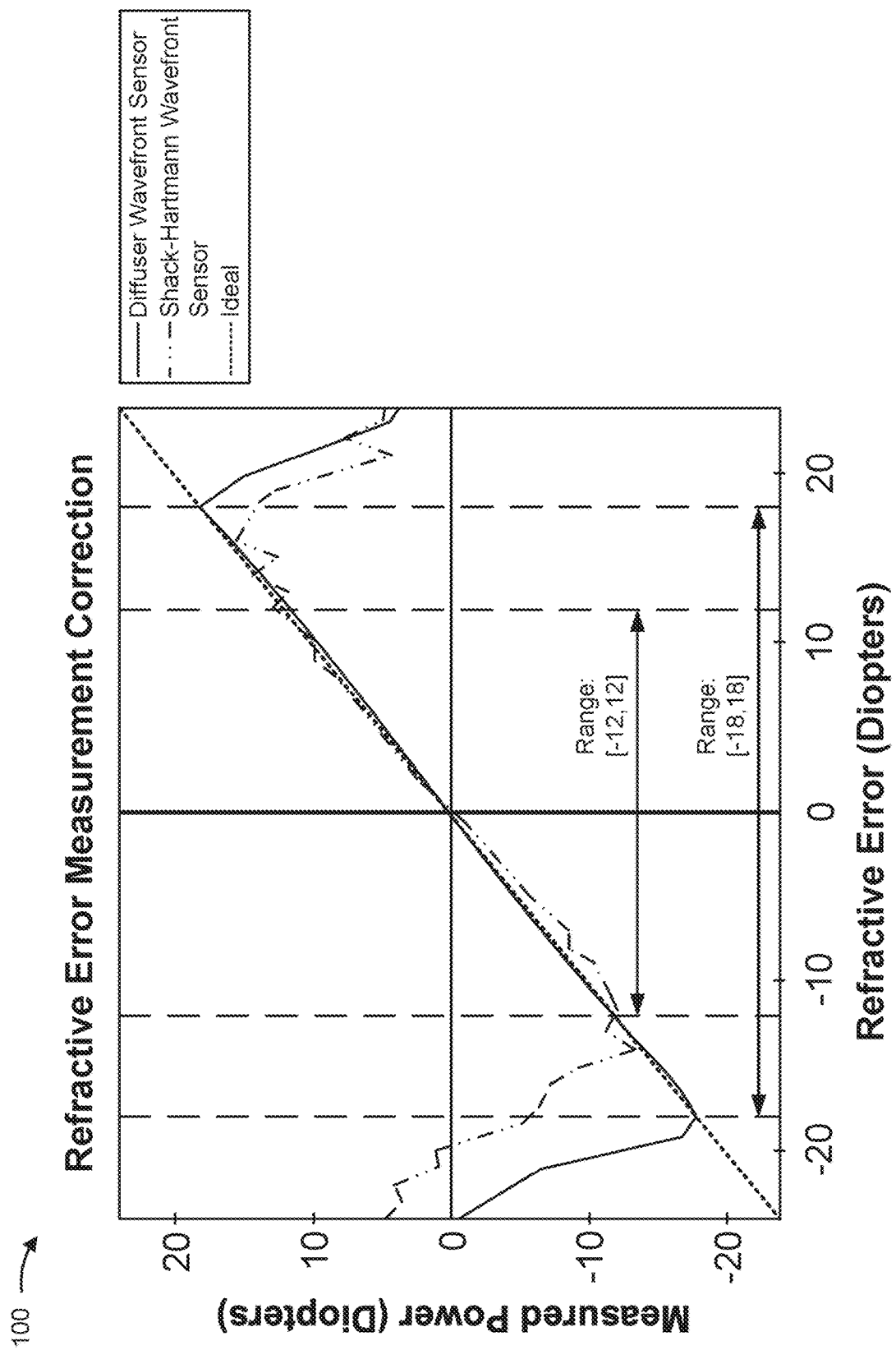

Diffuser wavefront sensor implementations, described herein, are capable of providing improved refractive error measurements. As shown in FIG. 1D, for example, the diffuser wavefront sensor is capable of measuring a larger range of refractive errors, and providing higher resolution measurements, than a typical wavefront sensor, such as a Shack-Hartmann wavefront sensor. Since each region of a diffuser-based caustic or speckle pattern is unique, it is possible to register large displacements of the caustic or speckle pattern, which permits for a larger measurable range than a pinhole- or lenslet-based wavefront sensor. For example, a typical Shack-Hartmann construction, where a beacon is illuminated on a retina, and an expensive lenslet array (e.g., two orders of magnitude more expensive than a diffuser) is utilized to measure a wavefront of light remitted from a pupil of an eye, may provide measurements in a range of about −12 diopters (D) of myopia to about ±12 D of hyperopia, with an accuracy of about ±0.25 D. In contrast, a wavefront sensor that utilizes a diffuser (which is relatively inexpensive compared to a lenslet array), as described herein, may provide measurements in a larger range—e.g., from about −18 D to about +18 D—and with improved accuracy—e.g., from about +0.5 D to about +0.1 D (e.g., within 0.125 D accuracy), which is a substantial improvement in prescription accuracy, given that eyeglasses are prescribed in 0.25 D increments.

Figure 1E:
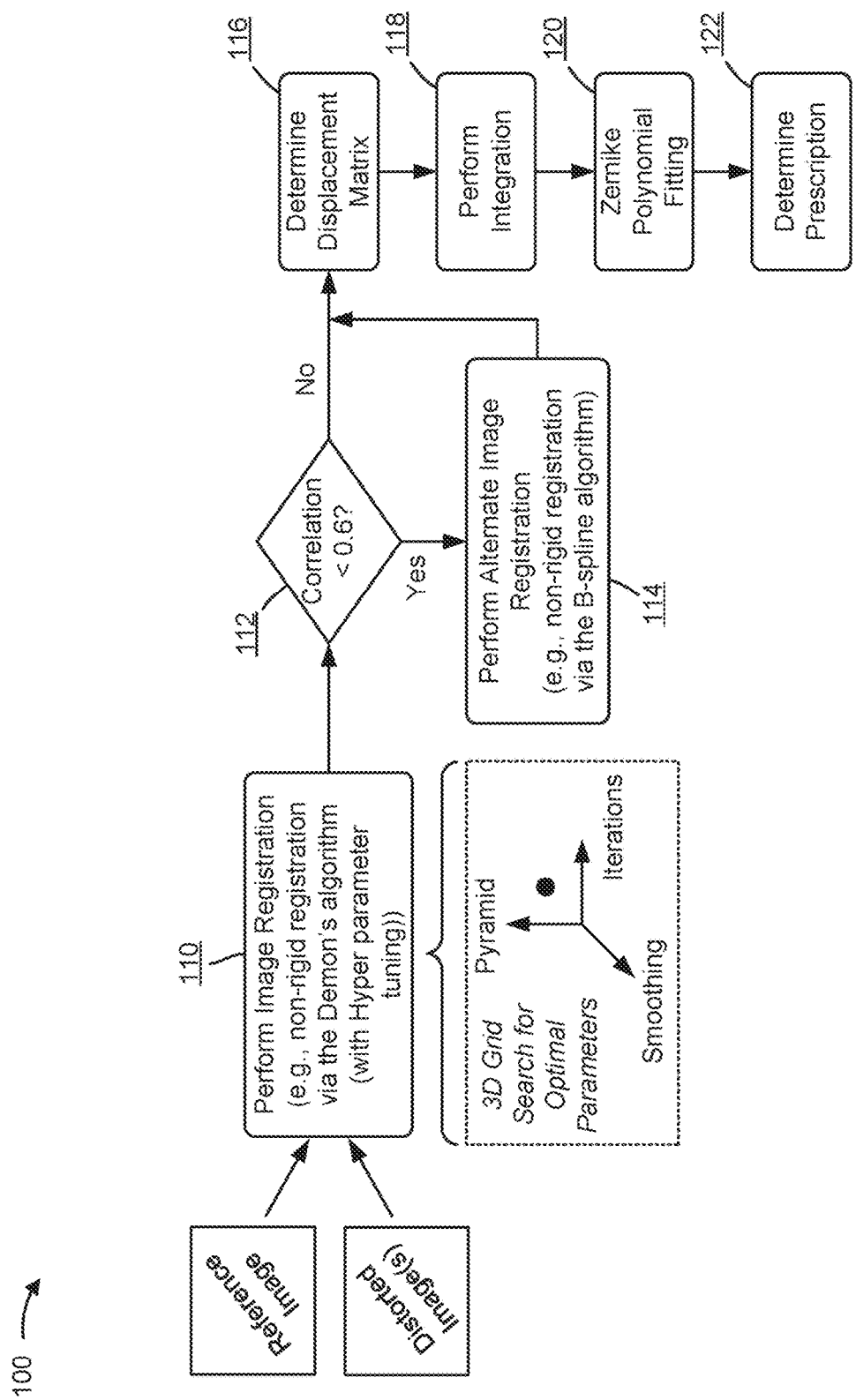

FIG. 1E is a diagram of a process for determining a prescription (e.g., an eyeglass prescription and/or the like) for correcting refractive errors of a patient's eye. In some implementations, the process may be performed by the diffuser wavefront sensor shown in FIGS. 1A and/or 1B and/or one or more additional devices and/or systems included in, or accessible to, the diffuser wavefront sensor.

As shown in FIG. 1E, and as shown by reference number 110, the process may include performing image registration of the distorted image(s) and a reference image (e.g., those described above in connection with FIGS. 1A to 1C) using one or more registration algorithms (e.g., a fast and robust image registration algorithm for phase measurements). For example, the registration algorithm may include one or more non-rigid registration algorithms, such as the Demon's algorithm (e.g., including hyperparameter tuning). As shown in FIG. 1E, the registration algorithm may include a three-dimensional (3D) grid search for optimal parameters—e.g., pyramid levels (e.g., relating to image sharpening), a quantity of algorithm iterations (e.g., relating to attempts to register the reference image and the distorted image(s)), and smoothing parameters (e.g., relating to the amount of smoothing needed for optimal registration of the images)—needed for efficient image registration. In some implementations, and as an alternative to utilizing a 3D grid search, the process may employ an optimization algorithm that identifies the optimal parameters (e.g., using a single optimization objective function with an appropriate solver).

As shown by reference number 112, the process may include determining whether a correlation, between the reference image and the distorted image(s), satisfies a threshold (e.g., is less than 0.6 and/or the like). If it is determined that the correlation satisfies the threshold, (reference number 112—YES), as shown by reference number 114, the process may include performing an alternate image registration procedure, such as non-rigid registration via one or more other algorithms. For example, in a case where the Demon's algorithm fails (e.g., is incapable of properly registering the reference image and the distorted image(s), such as may be the case if a patient needs high-power lenses), an alternate registration algorithm, such as the B-spline algorithm, the (1+1) evolutionary optimization algorithm, and/or the like, may be utilized.

After registration, as shown by reference number 116, the process may include determining a displacement matrix. For example, the process may include determining a matrix based on distances between pixels in the reference image and pixels in the distorted image(s). In some implementations, the displacement matrix may represent the transverse phase gradient of the aberrated wavefront, and may be integrated and fit to Zernike polynomials. For example, as shown by reference number 118, the process may include performing an integration of the displacement matrix (e.g., a circular integration across a radial axis). As shown by reference number 120, the process may include performing Zernike polynomial fitting, and as shown by reference number 122, the process may include determining a prescription (e.g., an eyeglass prescription) based on a result of the Zernike polynomial fitting. As an example, an eyeglass prescription may be determined from the low-order Zernike coefficients in accordance with the following:

$$D_{sphere} = \frac{-4\sqrt{3}\, C_2^0}{r_p^2},\ D_{cylinder, 0°} = \frac{-2\sqrt{6}\, C_2^2}{r_p^2},\ \text{and}\ D_{cylinder, 45°} = \frac{-2\sqrt{6}\, C_3^{-3}}{r_p^2}$$

where $C_n^m$ represents the Zernike coefficient of an $n^{th}$ radial and $m^{th}$ azimuthal degree Zernike polynomial fit to the aberrated wavefront, and $r_p$ represents a radius of a pupil. In some implementations, the parameters for the eyeglass prescription may be calculated by incorporating information from higher order aberrations, or by features learned from the caustic or speckle pattern by machine learning.

In this way, a relatively inexpensive diffuser-based wavefront sensor may be utilized, in conjunction with non-rigid registration, to determine a precise eyeglass prescription for a patient's eye, without a need for a trained eye care provider.

In some implementations, the process may employ an artificial intelligence technique, such as machine learning, deep learning, and/or the like to perform image registration and/or Zernike polynomial fitting. For example, the process may include training a model to perform image registration and/or Zernike polynomial fitting. The process may include training the model with a training dataset that includes pairs of Zernike coefficients and corresponding phase maps. In some implementations, the process may include generating different wavefronts as a training dataset using a spatial light modulator (e.g., a two-dimensional array of LEDs, a deformable mirror, and/or the like) by varying a pitch, a phase, and/or the like. Additionally, or alternatively, the process may include training the model using simulated training data. For example, a simulated model of a diffuser may be used to simulate deformations of a caustic or speckle pattern based on different aberrations (e.g., a defocus aberration, an overexposure aberration, a noise aberration, and/or the like).

Figure 1F:
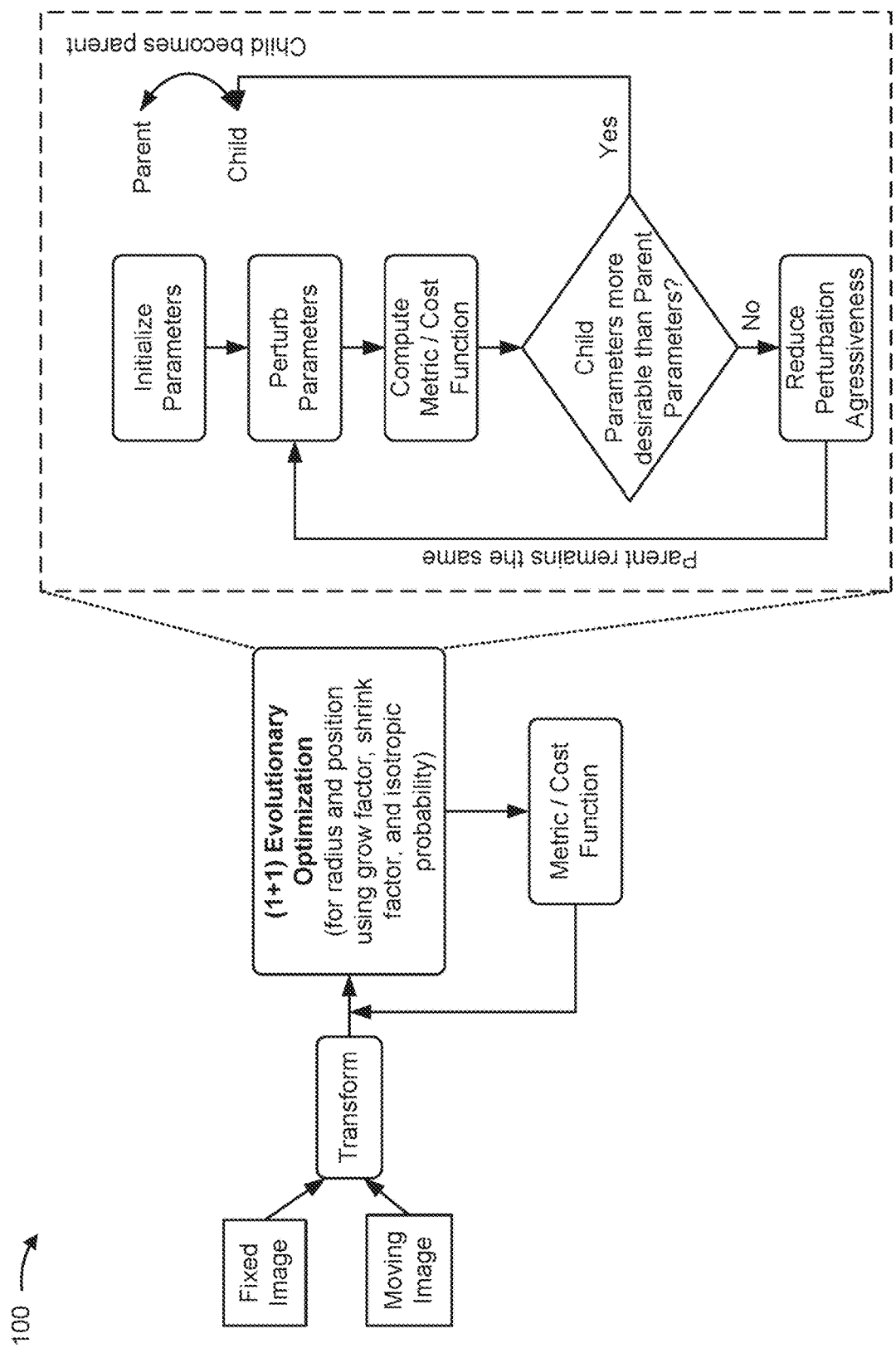

FIG. 1F is a diagram of an example process relating to the (1+1) evolutionary optimization algorithm, which may be used as an alternative to the above-described Demon's algorithm and the B-spline algorithm. Briefly, as shown in FIG. 1F, the process may involve providing a transformation, of a fixed image and a moving image, as input to the (1+1) evolutionary optimization algorithm. As further shown in FIG. 1F, the process may include initializing parent parameters, perturbing the parent parameters to derive child parameters, computing a metric/cost function, and determining whether the child parameters are more desirable than the parent parameters (e.g., are more suitable than the parent parameters in accordance with one or more metrics). If the child parameters are not more desirable than the parent parameters, the process may include reducing the perturbation aggressiveness, and returning to perturb the parent parameters. If the child parameters are more desirable than the parent parameters, the child parameters may replace the parent parameters, and the optimization process may repeat using the child parameters—e.g., by perturbing the child parameters, and so on until a certain threshold of a metric or cost function (e.g., structural similarity) is satisfied.

In some implementations, a diffuser-based ocular imaging system—e.g., a computational lightfield ophthalmoscope device—may be provided. The computational lightfield ophthalmoscope device may include a diffuser, an image sensor, multiple light sources (e.g., one or more LEDs, vertical-cavity surface-emitting lasers (VCSELs), laser diodes, and/or the like), and various associated components for simultaneously (or near simultaneously) measuring aberrations of a patient's eye and obtaining high-quality images (e.g., super-resolution images) of an anterior segment (e.g., the cornea) of a patient's eye and a posterior segment (e.g., the retina) of the patient's eye via spectral multiplexed measurements.

In some implementations, multiple light sources of different wavelengths may illuminate a patient's eye simultaneously, or nearly simultaneously, and a color camera that images the different caustic or speckle patterns formed by each light source may provide information about the chromatic aberrations of the eye. Multiple channels may also be used for reference channels relative to each other such that a reference image of an unaberrated wavefront is not needed. This information may be used for a more-precise eyeglass prescription calculation.

Figure 1G:
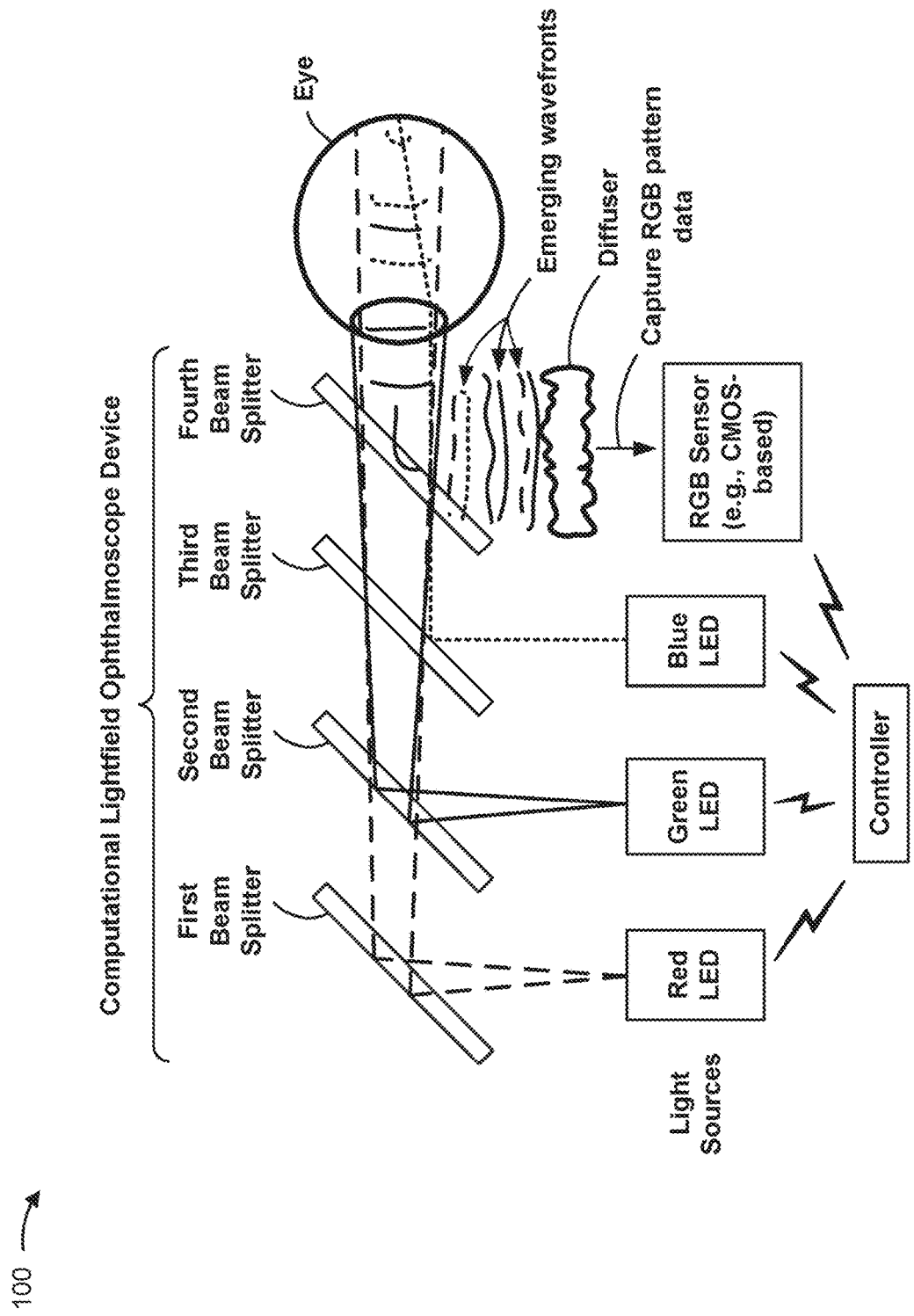

FIG. 1G is a diagram of an example computational lightfield ophthalmoscope device. As shown in FIG. 1G, the computational lightfield ophthalmoscope device may include multiple light sources—e.g., an LED configured to generate light in a wavelength range corresponding to the color red (a red LED), an LED configured to generate light in a wavelength range corresponding to the color green (a green LED), and an LED configured to generate light in a wavelength range corresponding to the color blue (a blue LED). In some implementations, the computational lightfield ophthalmoscope may include LEDs configured to generate light in other wavelength ranges (e.g., corresponding to different colors). As shown, the computational lightfield ophthalmoscope device may further include multiple beam splitters, a diffuser (e.g., the same as, or similar to, the diffuser described above in connection with FIGS. 1A and/or 1B), and an image sensor—e.g., here, a red-green-blue (RGB) sensor (e.g., a CMOS-based sensor).

In operation, blue light, green light, and red light may be simultaneously (or near simultaneously, e.g., within less than 1 minute, 1 second, 0.1 seconds, and/or the like) or sequentially outputted from the respective LEDs, reflected by respective beam splitters, and directed to various portions of a patient's eye. As shown in FIG. 1G, red light (e.g., having a certain beam width sufficient to illuminate an entirety of a posterior segment of the patient's eye, such as an entirety of the fundus, including the retina, the optic disc, the macula, the fovea, and/or the posterior pole) may be outputted from the red LED, reflected by a first beam splitter, and directed through a second beam splitter, a third beam splitter, and a fourth beam splitter toward the patient's eye. As shown, the red light may enter the patient's eye, and be projected across a posterior segment of the patient's eye (e.g., across the retina for fundoscopy). As further shown in FIG. 1G, green light (e.g., having a certain beam width sufficient to illuminate an entirety of an anterior segment of the patient's eye, such as an entirety of the cornea) may be outputted from the green LED, reflected by the second beam splitter, and directed through the third beam splitter and the fourth beam splitter toward the patient's eye. As shown, the green light may be projected onto an anterior segment (e.g., the cornea) of the patient's eye (e.g., for imaging of the anterior segment). As further shown in FIG. 1G, blue light (e.g., having a beam width that is much narrower than that of the red light and the green light) may be outputted from the blue LED, reflected by the third beam splitter, and directed through the fourth beam splitter toward the patient's eye. As shown, the blue light may enter the patient's eye, and be focused, in the form of a narrow light beacon, on a point in a posterior segment (e.g., the retina) of the patient's eye (e.g., to form a guide star for aberrometry). As further shown in FIG. 1G, the red light, the green light, and the blue light may be reflected and/or remitted from the patient's eye as emerging wavefronts, and may reflect off of the fourth beam splitter towards the diffuser, which may affect the emerging wavefronts and provide individual caustic or speckle patterns. As shown, the RGB sensor may capture image(s) of such caustic or speckle patterns, which may be subsequently processed (e.g., as described in more detail below). Employing a multi-channel image sensor, such as an RGB sensor, to capture images of multiple caustic or speckle patterns, based on multiplexing of multiple light channels, enables simultaneous (or near simultaneous) or sequential, and synergistic, measurements of aberrations of a patient's eye and generation of high-quality images of anterior and/or posterior segments of the patient's eye.

In various implementations, the computational lightfield ophthalmoscope device may include, or have access to, a processor (e.g., one or more processor devices or hardcore reconfigurable devices, such as a field-programmable gate arrays (FPGAs), a portable graphics processing unit (GPU), and/or the like), memory, a power source (e.g., for powering various components of the computational lightfield ophthalmoscope device), electric/electronic circuitry (e.g., regulator(s) and/or the like), and/or the like—e.g., some, or all, of these components may be included in the controller shown in FIG. 1G. In some implementations, the processor may be configured (e.g., based on programmed instructions, based on an input by a user, such as a patient, and/or the like) to provide overall control of the computational lightfield ophthalmoscope device, including, for example, operation of the light sources, the image sensor, and/or the like.

Although not shown, in various implementations, the computational lightfield ophthalmoscope device may include one or more user interfaces (e.g., including a capacitive touch screen, a keypad, button(s), and/or the like) configured to enable a user (e.g., a patient) to interact with the computational lightfield ophthalmoscope device, such as to input instructions for initiating an eye exam using the computational lightfield ophthalmoscope device. In some implementations, the user interface(s) may include a display configured to display information regarding one or more results of an eye exam (e.g., prescription information, clinical screening information, and/or the like). In some implementations, the computational lightfield ophthalmoscope device may include a communication interface configured to permit data exchange with one or more external systems (e.g., external systems for reviewing the prescription information, the clinical screening information, and/or the like).

Although not shown, in some implementations, the computational lightfield ophthalmoscope device may be implemented as a scope-like (e.g., open-view) device that permits a patient to view through the computational lightfield ophthalmoscope device (e.g., through the arrangement of beam splitter(s) and/or the like) into the environment. This permits a patient to focus, through the computational lightfield ophthalmoscope device, the patient's view on a static or mobile object (e.g., a tree, picture, and/or the like), which enables varied and flexible measurements to be made during examination.

Figure 1H:
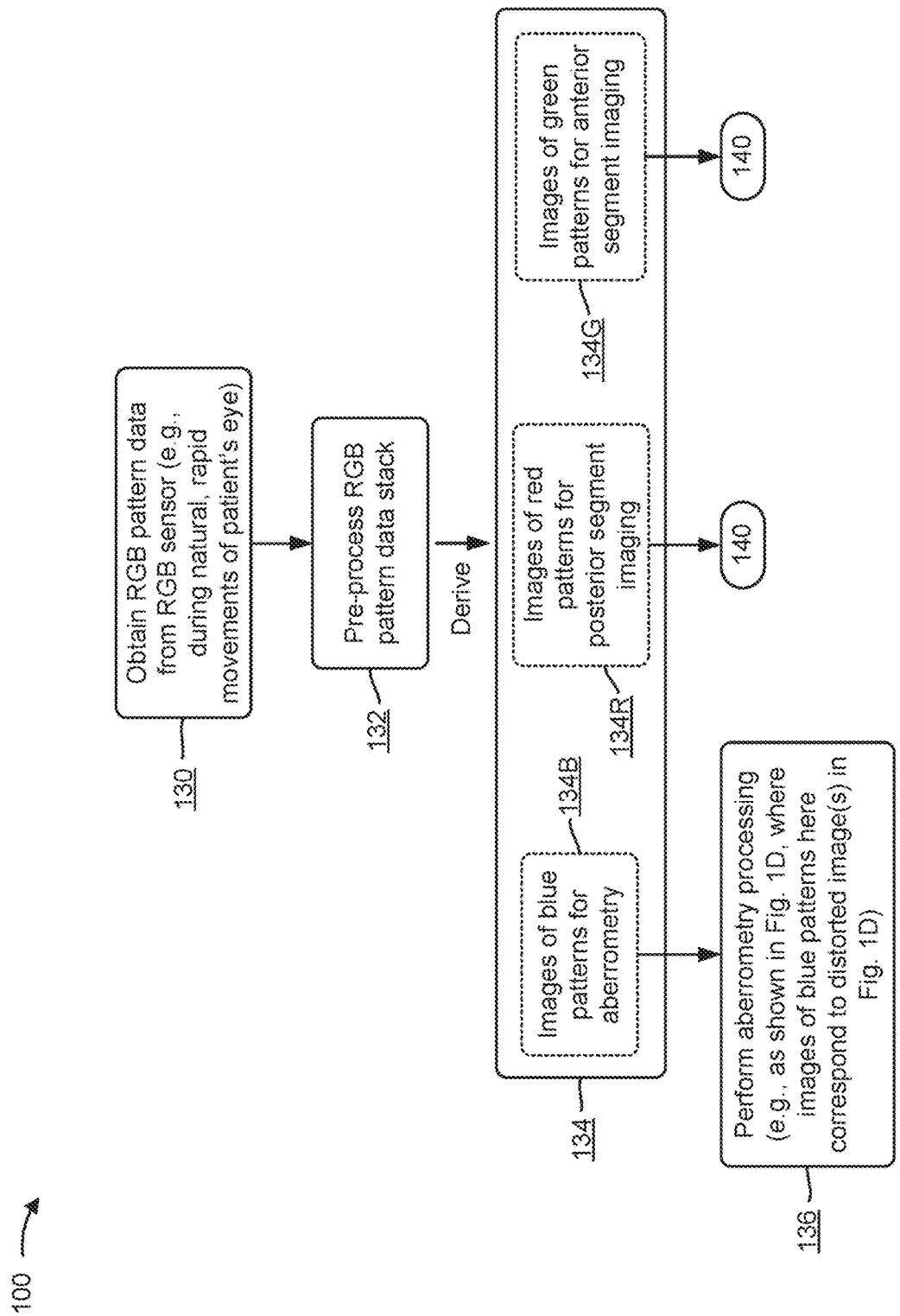
Figure 1I:
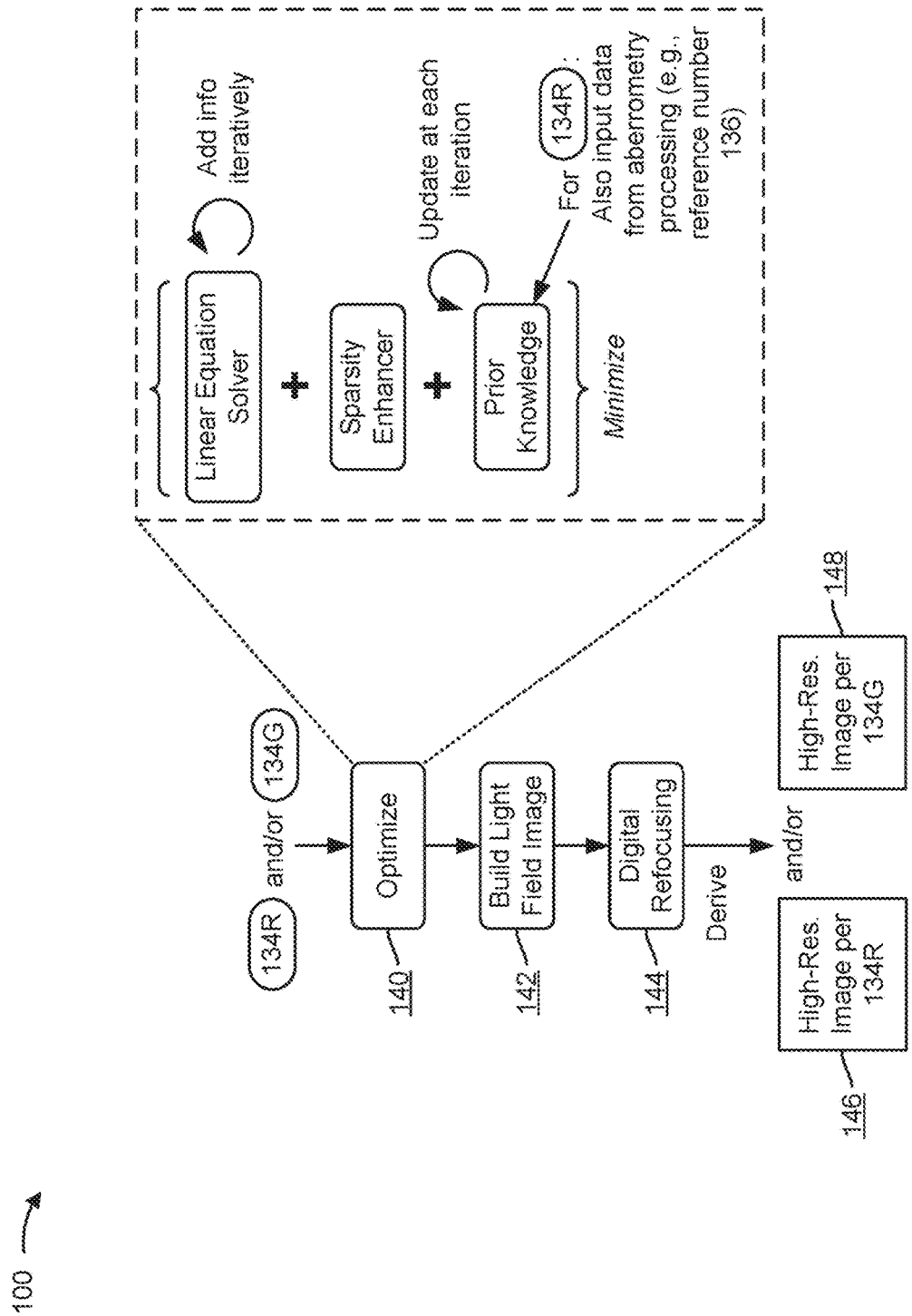

FIGS. 1H and 1I are diagrams of a process for simultaneous (or near simultaneous) aberrometry and contactless imaging of a patient's eye. In some implementations, the process may be performed by the computational lightfield ophthalmoscope device shown in FIG. 1G (e.g., by the processor, based on programmed instructions, based on an input by a user, such as a patient, and/or the like) and/or one or more additional devices and/or systems included in, or accessible to, the computational lightfield ophthalmoscope device.

As shown in FIG. 1H, and shown by reference number 130, the process may include obtaining RGB caustic or speckle pattern data. For example, the process may include obtaining RGB caustic or speckle pattern data from the RGB sensor described above in connection with FIG. 1G. In some implementations, the RGB sensor may be configured to capture image(s) of caustic or speckle patterns, provided by the diffuser, while a patient's eye is moving. For example, an eye exhibits small and random, natural movements, and thus capturing a series of images (e.g., high-speed, simultaneous, lens-less images) of the anterior segment (e.g., the cornea) and the posterior segment (e.g., the retina) of the patient's eye enables reconstruction, from the series of captured images, of higher resolution images (e.g., high-quality, three-dimensional (3D) images). As another example, and even in a case where objects (e.g., the cornea and/or the retina) may be static in a series of captured images, other changes, such as changes to detected wavefronts, may also be exploited for high-resolution image reconstruction purposes.

In some implementations, one or more algorithms (e.g., a neural network) may be trained to identify, in image(s) of caustic or speckle pattern(s) relating to the retina, features that directly map to refractive errors or ocular pathologies. Using image(s) of caustic or speckle pattern(s) here, rather than high-resolution image reconstructions, may, for example, permit for faster and/or more manageable analysis of large datasets and/or a suitable forward model that allows for derivation of large datasets of synthetic data.

As shown by reference numbers 132 and 134, the process may include pre-processing an RGB caustic or speckle pattern data stack to derive images of the individual caustic or speckle patterns corresponding to the various light sources. As shown by reference number 134B, images of caustic or speckle patterns corresponding to the blue light may be derived and used for aberrometry. As shown by reference number 136, the process may include performing aberrometry processing (e.g., the aberrometry processing described above in connection with FIG. 1E) using the image(s) of the caustic or speckle pattern(s) corresponding to the blue light. As shown, images of caustic or speckle patterns corresponding to the red light (images 134R) may be derived and used for posterior segment (e.g., retinal) imaging, and images of caustic or speckle patterns corresponding to the green light (images 134G) may be derived and used for anterior segment (e.g., corneal) imaging. For example, images 134R (of the caustic or speckle patterns corresponding to the red light) may represent sparse images that are to undergo reconstruction (e.g., which may involve leveraging a sparsity enhancement operator to iteratively refine spatially distance patches within a reconstruction), and images 134G (of the caustic or speckle patterns corresponding to the green light) may similarly represent sparse images that are to undergo reconstruction. In some implementations, the process may include utilizing one or more regularization parameters to reconstruct a high-resolution image reconstruction of a retina based on images 134R, and similarly reconstruct a high-resolution image reconstruction of a cornea based on images 134G (e.g., similar to that which may be performed in computed tomography (CT) reconstruction (e.g., including error reduction processing, compressed sensing techniques involving wavelet coefficients, and/or the like, as described in more detail below)).

In some implementations, a reconstruction algorithm may be provided to derive high-resolution images based on images 134R and/or images 134G. As shown in FIG. 1I, and as shown by reference number 140, the reconstruction algorithm may include an optimization process (e.g., a forward-backward primal dual optimization process) that leverages a linear equation solver, a sparsity enhancer, and prior knowledge. In some implementations, the optimization process may operate on images 134R for purposes of deriving a high-resolution image reconstruction of the retina, and may be separately leveraged to operate on images 134G for purposes of deriving a high-resolution image reconstruction of the cornea. In some implementations, and in a case where the optimization process operates on images 134R, the prior knowledge may include data obtained from the aberrometry processing (e.g., reference number 136), such as prescription information determined based on measurements of aberrations of a patient's eye. Utilizing this prescription information, in the optimization process for images 134R, enables the derivation of aberration-corrected images of the retina, which improves overall retinal imaging quality.

As shown by reference number 142, the reconstruction algorithm may include building a light field image based on outputs of the optimization process (e.g., by restructuring vector-based outputs of the optimization process, as described in more detail below). As shown by reference number 144, the reconstruction algorithm may include digitally refocusing of the light field image to derive a high-resolution image reconstruction (e.g., a high-resolution image reconstruction 146 of the retina, in a case where reconstruction is based on images 134R, or a high-resolution image reconstruction 148 of the cornea, in a case where reconstruction is based on images 134G). Here, since the target object—e.g., the retina or the cornea—has a curved (rather than a flat) surface, digital refocusing may be needed in order to reconstruct a sharp, high-quality image of the object that is useful for clinical screening. In some implementations, digital refocusing may involve a sharpness maximization algorithm that is executed for each pixel in an image (e.g., such that a pixel, farther from a center pixel, may be associated with a different axial location than a pixel that is closer to the center pixel).

In some implementations, an artificial intelligence technique, such as machine learning, deep learning, and/or the like may be used to derive high-resolution images based on images 134R and/or images 134G (e.g., used to perform image reconstruction). For example, the process may include training a model to derive high-resolution images based on images 134R and/or images 134G. The process may include training the model with a training dataset that includes retinal images and associated diffuser patterns of the retinal images (e.g., diffuser patterns generated by the computational lightfield ophthalmoscope).

In some implementations, deep learning algorithms may be provided for automated clinical screening based on high-resolution image reconstructions 146 and/or 148 (e.g., for diagnosing diabetic retinopathy, macular edema, and/or the like). In some implementations, neural networks (e.g., adversarial networks and/or the like) may be utilized to generate large data sets of synthetic images for training and validation. In some implementations, temporal variations in speckle patterns may also be analyzed to assess intraocular pressure.

In this way, a single device equipped with light sources, an RGB sensor (e.g., a single camera), and a diffuser, may be used for both aberrometry and ocular imaging. This reduces or eliminates a need to use separate cameras or devices for aberration measurements and ocular imaging, which conserves costs, simplifies the overall eye examination process, and provides high-accuracy aberration measurements and high-quality ocular images for clinical screening.

In some implementations, the reconstruction algorithm described above may reconstruct a wide-field, high-resolution image from diffuser-based imaging, using multiple randomly perturbed measurements of a scene (e.g., such as images 134R). For example, where $b \in \mathbb{R}$ are the vectorized concatenated diffuser-based camera measurements, and $A \in \mathbb{R}$ is a sparse representation of the imaging system, a vectorized wide-field scene $x \in \mathbb{R}$ may be recovered from randomized measurements b. In some implementations, an optimization-based reconstruction and sparse recovery algorithm, which involves solving an inverse problem, may be used. In some implementations, the optimization-based reconstruction and sparse recovery algorithm may involve enhancing the sparsity by incorporating total variation terms and wavelet operators. Such an algorithm may be capable of incorporating prior knowledge regarding shape, color, and structure. In addition, learning-based algorithms may also be used to eliminate regularization uncertainties and to reduce computational burden.

In some cases, an effectiveness of the (wide-field image) reconstruction algorithm described above may be evaluated via a forward model for a diffuser to simulate diffuser-based camera images. Here, for example, a publicly-available diabetic retinopathy database may be used to simulate diffuser-based camera images for reconstruction via the reconstruction algorithm. In some cases, reconstructed images may be quantitatively evaluated using metrics, such as structural similarity index, Pompeiu-Hausdorff distance, and/or Fourier ring correlation. In some cases, reconstructed images may additionally, or alternatively, be qualitatively evaluated for diagnostic value—e.g., via a visual Turing test by an ophthalmologist.

In some cases, following a qualitative and quantitative evaluation of the reconstruction algorithm described above, a model eye may be utilized to tune the reconstruction algorithm (e.g., to tune hyper-parameters associated with the reconstruction algorithm). Such parameters may be tuned using extensive multidimensional grid search and log to linear variation methods, and then tested in a model eye.

In cases where reconstruction of a wide-field retinal image, for example, may not be possible from a standard diffuser, a large diffuser may be employed. In some implementations, the reconstruction algorithm described above may derive only a greyscale, high definition image of a retina, which may not have diagnostic features as compared to a color image. In such cases, a deep-learning-based transformation may be employed to derive a color image from the greyscale image. In some implementations, computationally complex operations in the reconstruction algorithm may be reduced by employing efficient optimization methods (e.g., primal dual methods).

In this way, a reconstruction algorithm may be provided that reconstructs a fundus image, from a diffuser-based camera image of both a simulated retina and a model eye, that may be classified as normal or pathological with reasonable accuracy. Moreover, the accuracy of such classifications may be improved through the use of attention mechanisms.

Figure 1J:
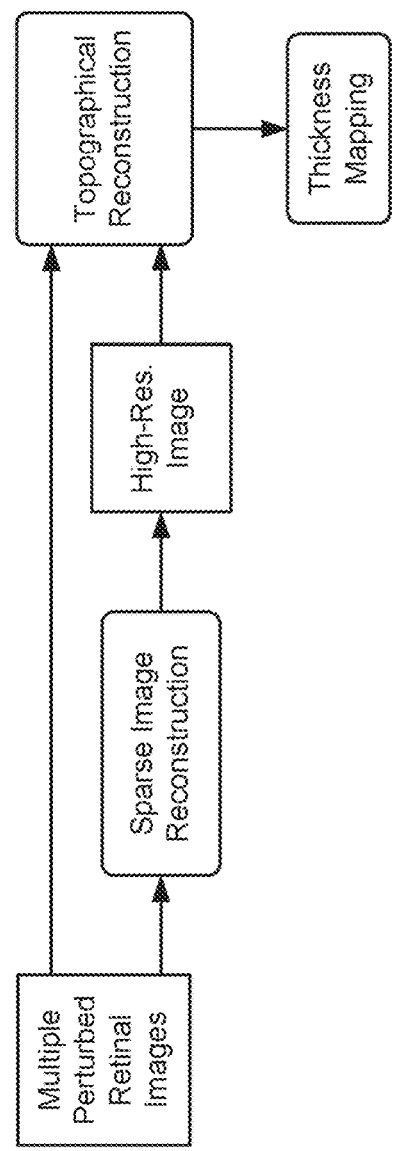

In some implementations, the topography of a surface of the retina may be reconstructed using a perturbed image stream by using deep learning techniques, adversarial training techniques, shape (or structure) from motion techniques, simultaneous localization and mapping techniques, and/or a combination of such techniques. As shown in FIG. 1J, multiple perturbed retinal images and a high-resolution of a retina may be utilized to reconstruct the topography of the surface of the retina, after which the reconstructed topography may be used to map retinal thickness. In various implementations, the reconstructed topography may be used to map retinal thickness via point-to-point distance approximation, optimization-based distance approximation, deep learning, adversarial training, dictionary learning, autoencoders, attention mechanisms, multiple instance learning, and/or a combination of such methods.

In some implementations, the computational lightfield ophthalmoscope device may be implemented in a variety of end products, including, for example, a commercial computational lightfield ophthalmoscope, a portable device (e.g., a smartphone-based device or a cell-phone-based), a lightfield ophthalmoscope, a high-range autorefractor, a wavefront sensor (e.g., for guiding laser-assisted in situ keratomileusis (Lasik) surgery), and/or the like.

Figure 1K:
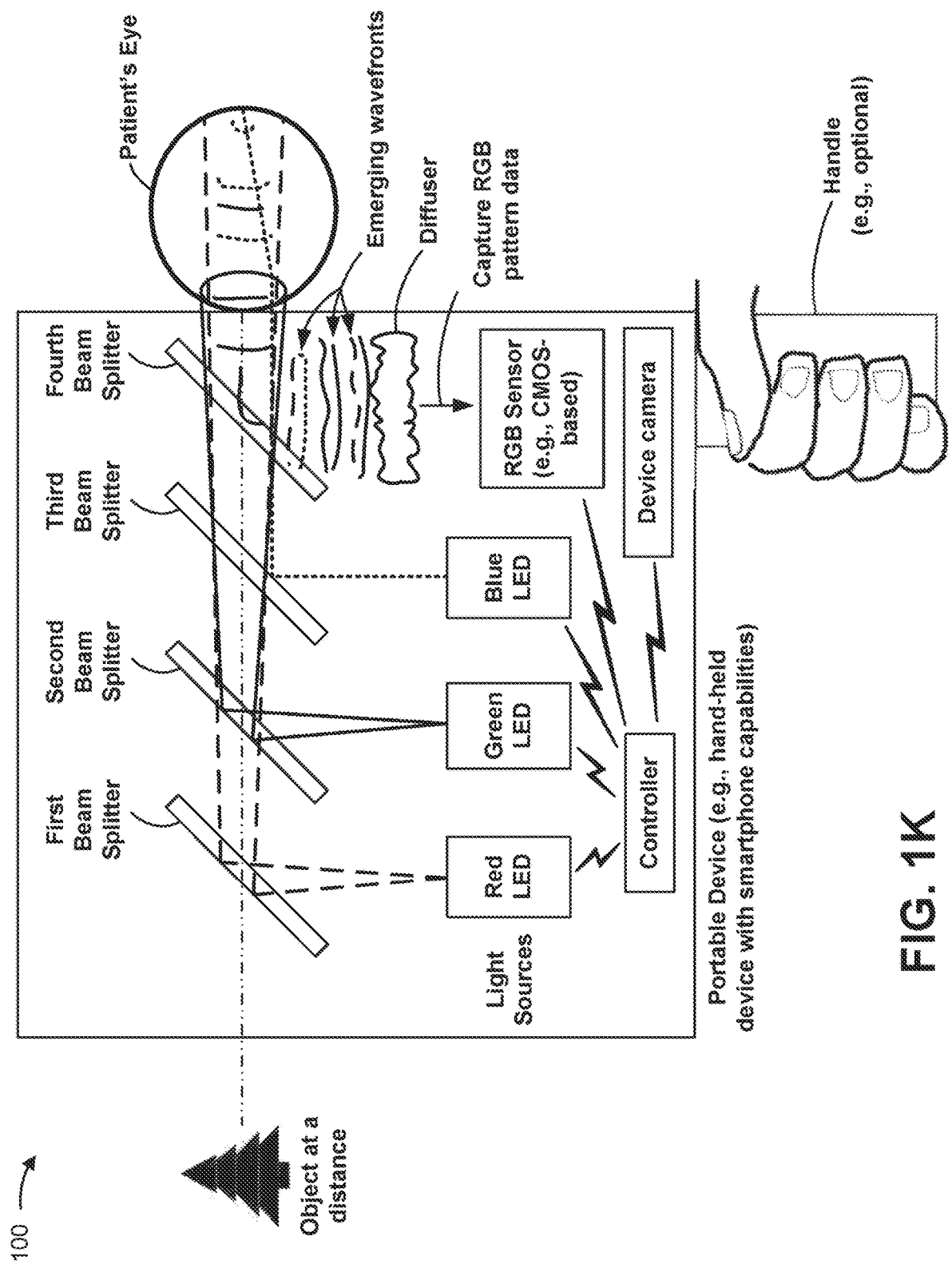

For example, in some implementations, the computational lightfield ophthalmoscope device may be implemented in a portable device (e.g., a hand-held device with smartphone capabilities and/or the like). FIG. 1K is a diagram showing a partial view of an example portable device that includes the computational lightfield ophthalmoscope device. As shown, the portable device may include various components of the computational lightfield ophthalmoscope device described above in connection with FIG. 1G (e.g., beam splitters, light sources, an RGB sensor, a diffuser, a controller, and/or the like). As shown in FIG. 1K, the portable device may be configured as a scope-like device (e.g., similar to that described above) that permits a patient to view through the portable device (e.g., through transparent viewing window(s), through the beam splitters, and/or the like) into the environment (e.g., to view object(s) at a distance). In some implementations, and as shown in FIG. 1K, the portable device may include a lens (e.g., for re-imaging caustic or speckle patterns provided by the diffuser), a device camera, and an optional handle for a user to hold and/or otherwise manipulate the portable device.

Figure 1L:
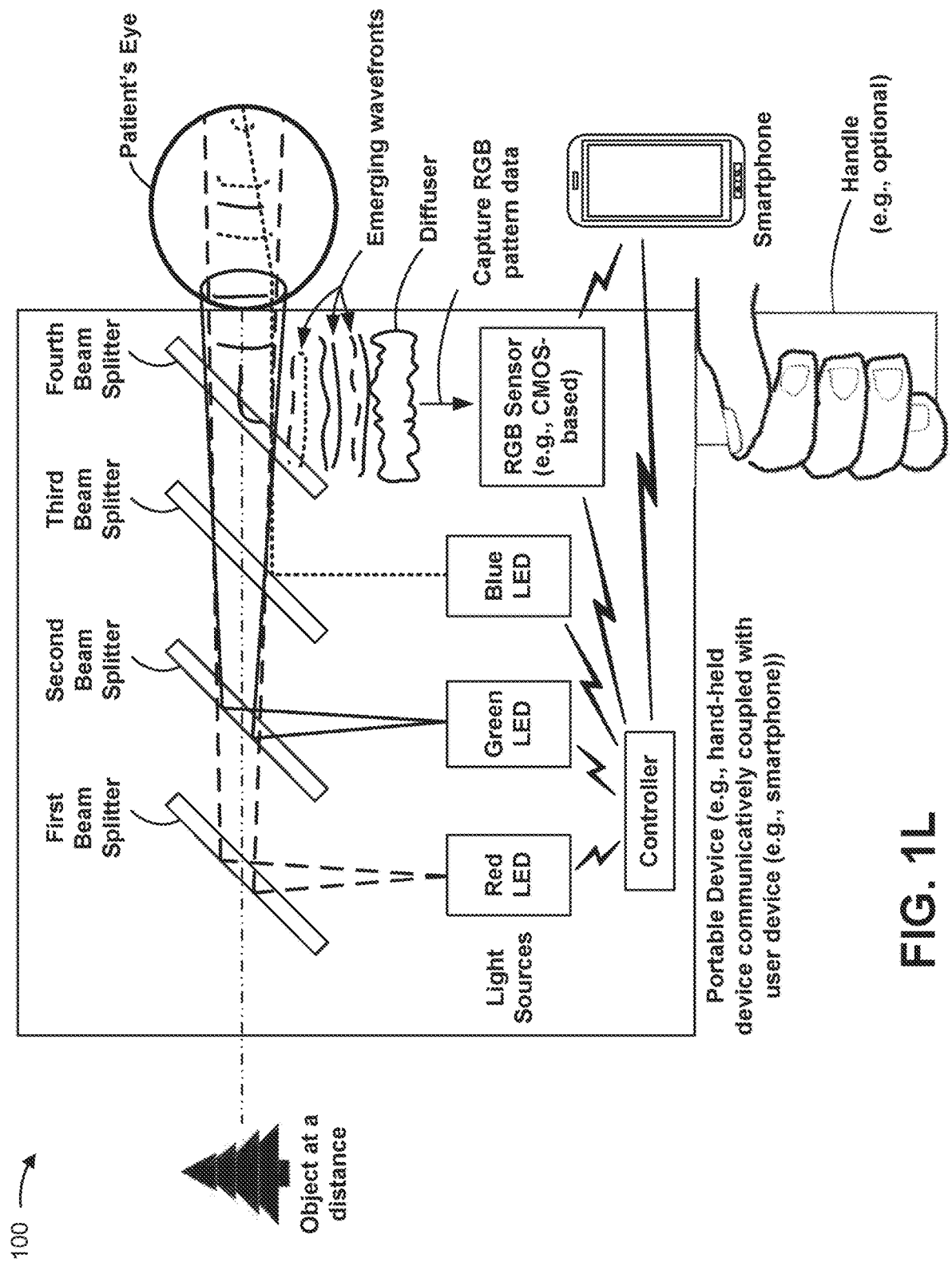

In some implementations, and as shown in FIG. 1L, the portable device may alternatively be configured to communicate with a user device—e.g., a mobile device, such as a smartphone. For example, the portable device may be configured to attach to (e.g., physically and communicatively couple to), and be compatible with, one of a variety of smartphone types. In some implementations, the RGB sensor may include a camera capable of providing images (e.g., wirelessly) to the smartphone for processing and analysis. In some implementations, a flash of the smartphone may be implemented as one or more of the light source(s), and may be routed to a patient's eye using mirrors and/or a light guide.

In this way, the computational lightfield ophthalmoscope device may be implemented in lightweight, portable form factors, which permits widespread distribution of the computational lightfield ophthalmoscope device to a large quantity of users for self-administered, simultaneous aberrometry and ocular imaging without a need for a trained eye care provider.

In some implementations, the image sensor of the computational lightfield ophthalmoscope device may be positioned in a plane (e.g., at a location), relative to the diffuser, where an image sharpness, of a caustic or speckle pattern provided by the diffuser, satisfies a threshold (e.g., is sharp or sharpest). The location may be determined, for example, by transmitting a planar wavefront to the diffuser, and axially adjusting a position of the image sensor and/or the diffuser until a caustic or speckle pattern imaged by the image sensor is sharp or sharpest.

Additionally, or alternatively, and in some implementations, a tunable lens (e.g., included in, or provided by, a device in which the computational lightfield ophthalmoscope device is implemented, such as a portable device and/or the like) may be positioned between the diffuser and the image sensor to permit adjustment of a conjugate imaging plane of the image sensor to different positions relative to the diffuser. This permits sweeping (e.g., volumetric sampling) of imaging planes to identify a plane where an image of the caustic or speckle pattern is sharp (or sharpest), which allows for signal-to-noise ratio optimization. This is particularly beneficial, since such a plane may be different for myopic (nearsighted) patients and hyperopic (farsighted) patients.

In some cases, light (directed toward a patient's eye) and/or caustic or speckle patterns, may result in corneal reflections, which may negatively impact a signal-to-noise ratio of an image sensor. Thus, in some implementations, the computational lightfield ophthalmoscope device may include one or more components configured to block such corneal reflections. In some implementations, the component(s) may include one or more apertures defined and arranged at one or more locations that permit some light to pass through, and reject remaining light. This permits, for example, sampling, at the image sensor, of only a beacon remitted by the retina of a patient's eye.

In some implementations, one or more light sources of the computational lightfield ophthalmoscope device may include one or more speckle reducers (e.g., laser speckle reducers). A speckle reducer may include an oscillating diffuser, a laser diode that is capable of power oscillation, a superluminescent diode, and/or the like. In some implementations, the computational lightfield ophthalmoscope device may include one or more additional diffusers (e.g., laser speckle reducers and/or the like) positioned in front of each light source (e.g., a certain distance from a light emitting portion of the light source) to assist with reducing speckle patterns.

In some implementations, rather than employing light sensors that emit light of different colors (e.g., in the spectral multiplexing implementation of the computational lightfield ophthalmoscope device described above in connection with FIG. 1G), the computational lightfield ophthalmoscope device may include multiple light sensors configured to emit light in the same wavelength range, and a monochrome image sensor (e.g., a monochrome camera) configured to detect light in that wavelength range. In such cases, the computational lightfield ophthalmoscope device may be configured to obtain temporal multiplexed measurements— e.g., by controlling the various light sensors to emit light at different spatial frequencies (e.g., a first light source may periodically emit light at one frequency (e.g., 3 Hertz (Hz) and/or the like), a second light source may periodically emit light at another frequency (e.g., 5 Hz and/or the like), and a third light source may periodically emit light at yet another frequency (e.g., 15 Hz and/or the like)) so as to obtain various sources of contrast in a video set. Here, images of the caustic or speckle patterns, obtained by the monochrome image sensor, may be processed to measure aberrations of a patient's eye and generate high-quality images of anterior and posterior segments of the patient's eye.

In some implementations, a size of the diffuser may be defined to enable capturing of various portions of a posterior segment of a patient's eye. For example, a diffuser having a larger length may enable capturing of higher numerical aperture images of the retina, and thus higher quality images of the retina for purposes of diagnosing diseases and/or the like.

In some implementations, the image sensor may capture multiple images of light reflected and/or remitted from a patient's eye (e.g., as caustic or speckle patterns). For example, the image sensor may capture multiple images from different perspectives (e.g., angles). The multiple images may be captured as discrete images or as a video composed of multiple frames (e.g., a frame of the video may correspond to a discrete image). The multiple images may be combined (e.g., mosaicked) to form a single image of a caustic or speckle pattern. In this way, the single image formed from the multiple images provides a larger field of view.

In some implementations, the computational lightfield ophthalmoscope may include, or be used in connection with, one or more secondary light sources. A secondary light source may be configured on the computational lightfield ophthalmoscope, such that the secondary light source corresponds to a temple area of a patient during use of the computational lightfield ophthalmoscope. Alternatively, the secondary light source may be separate from the computational lightfield ophthalmoscope (e.g., a flashlight) and held to a temple area of a patient during use of the computational lightfield ophthalmoscope (e.g., when capturing an image of light reflected and/or remitted from the patient's eye). In this way, the secondary light source provides transcranial illumination that provides even illumination of a fundus.

In some implementations, to permit rapid image registration and/or rapid image reconstruction (e.g., using the registration algorithm(s) and/or the reconstruction algorithm(s) described above in connection with FIGS. 1E, 1H, and 1I), the computational lightfield ophthalmoscope device may include one or more low-powered GPUs, FPGAs, and/or the like configured to implement the registration algorithm(s), the reconstruction algorithm(s), a machine learning model, and/or the like in real-time (or near real-time) so as to provide a high-speed, computationally-efficient system.

In this way, all objective measurements of a comprehensive ocular exam may be provided using a single device or system. Employing a single computational lightfield ophthalmoscope device, such as that described herein, is advantageous over existing ocular examination instrumentation, since a single device can be used for refraction examination and imaging of anterior and posterior segments of a patient's eye. This reduces or eliminates a need to utilize three prior, complex systems (i.e., an autorefractor, a traditional ophthalmoscope, and a slit lamp) to conduct an eye exam, which simplifies, and reduces the costs of, such exams, thereby making affordable eye care accessible to more people. Additionally, a device that includes a minimal quantity of components—e.g., a light source (e.g., a light-emitting diode), a diffuser, and an image sensor, as described herein—and that provides objective measurements, reduces or eliminates a need for trained eye care providers to conduct eye exams, which also reduces the costs, and improves the overall accuracy, of such exams, thereby yielding more precise eyeglass prescriptions. Furthermore, utilizing a device, as described herein, provides synergistic measurements—e.g., wavefront information may be used to reconstruct higher quality retinal images, and such retinal images may be used to inform aberration measurements. This reduces or eliminates a need to utilize expensive closed-loop adaptive optics systems that may otherwise be needed to obtain high-resolution retinal images. High-resolution images of the fundus, provided by implementations described herein, also enable applications beyond eye examinations, including the assessment of various conditions relating to the brain (e.g., stroke severity, brain injury, neurodegenerative diseases, and/or the like), given that the retina may be a non-invasive portal to the brain. Such images of the fundus may also enable the assessment of a variety of health metrics, including, for example, blood pressure, cardiovascular risk factors, age, and/or the like.

As indicated above, FIGS. 1A-1L are provided merely as examples. Other examples are possible and may differ from what was described with regard to FIGS. 1A-1L.

Figure 2:
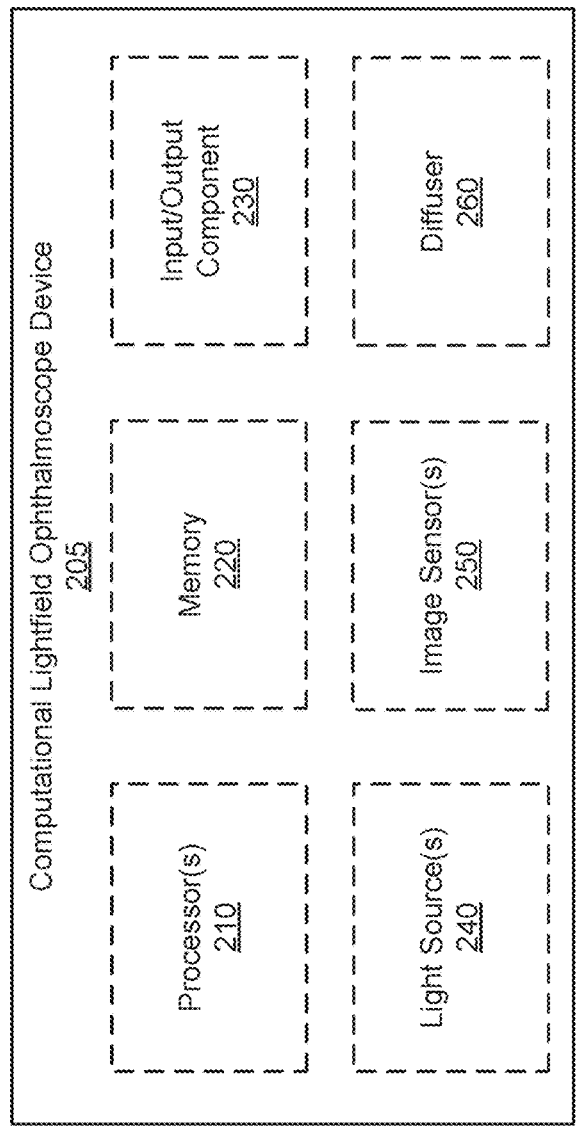
FIG. 2 is a diagram of an example environment in which systems and/or methods, described herein, may be implemented.
Figure 2:
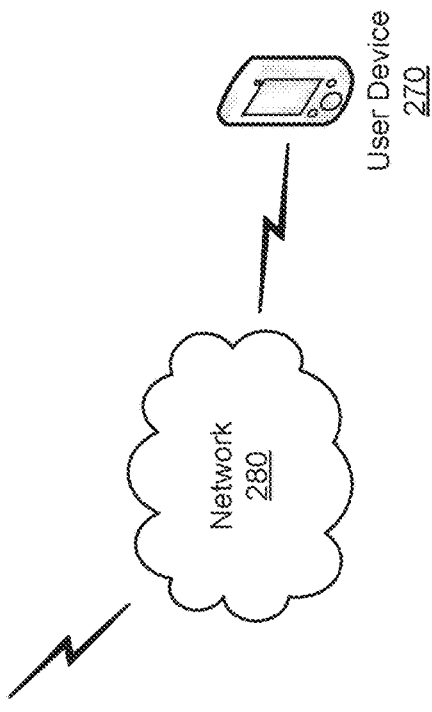

FIG. 2 is a diagram of an example environment 200 in which systems and/or methods described herein may be implemented. As shown in FIG. 2, environment 200 may include a computational lightfield ophthalmoscope device 205 (that includes various components and/or devices), a user device 270, and a network 280. Devices of environment 200 may interconnect via wired connections, wireless connections, or a combination of wired and wireless connections.

Processor(s) 210 include one or more types of processing components capable of being programmed to perform a function, such as one or more operations described elsewhere herein. For example, processor(s) 210 may be configured to facilitate process 400 of FIG. 4 and/or the like. In some implementations, processor(s) 210 may (e.g., based on programmed instructions, user input, and/or the like) control one or more light sources (e.g., light source(s) 240) to emit light and one or more image sensors (e.g., image sensor(s) 250) to capture images, as described elsewhere herein. Processor(s) 210 corresponds to a processor, described in more detail below in connection with FIG. 3.

Memory 220 includes one or more types of memories capable of storing information. In some implementations, memory 220 may store information associated with performing one or more operations described elsewhere herein. For example, memory 220 may store information to be used (e.g., by processor(s) 210) to facilitate process 400 of FIG. 4 and/or the like. In some implementations, memory 220 may correspond to a memory or storage component, described in more detail below in connection with FIG. 3.

Input/output component 230 includes one or more components capable of being used to input information into, and/or output information from, computational lightfield ophthalmoscope device 205. In some implementations, input/output component 230 may include one or more touch screen components, one or more keypads, one or more buttons, and/or the like. In some implementations, input/output component 230 may include one or more user interfaces configured to permit a user to interact with computational lightfield ophthalmoscope device 205, as described elsewhere herein. In some implementations, input/output component 230 may correspond to an input component and an output component, described in more detail below in connection with FIG. 3.

Light source(s) 240 include one or more devices capable of emitting light. For example, light source(s) 240 may include one or more LEDs, VCSELs, laser diodes, and/or the like. In some implementations, light source(s) 240 may include one or more devices capable of emitting light in different wavelength ranges (e.g., corresponding to different colors), such as red, green, blue, and/or the like, for purposes of obtaining aberrometry measurements and high-resolution images of anterior and posterior segments of a patient's eye, as described elsewhere herein.

Image sensor(s) 250 include one or more devices capable of capturing images. For example, image sensor(s) 250 may include a CMOS-based sensor and/or the like configured to detect light in one or more ranges of wavelengths (e.g., wavelengths corresponding to light that may be emitted by light source(s) 240). In some implementations, image sensor(s) 250 may include an RGB sensor capable of capturing images of caustic or speckle patterns, provided by a diffuser (e.g., diffuser 260), for purposes of obtaining aberrometry measurements and high-resolution images of anterior and posterior segments of a patient's eye, as described elsewhere herein. In some implementations, image sensor(s) 250 may include a camera in a mobile phone. In some implementations, computational lightfield ophthalmoscope device 205 may be configured to attach to (e.g., physically and communicatively couple to), and be compatible with, one of a variety of mobile phone types. In some implementations, light source(s) 240 may include a flash from a mobile phone, which may be routed to a patient's eye using mirrors and/or a light guide.

Diffuser 260 includes one or more devices capable of diffusing light. For example, diffuser 260 may be composed of one or more materials capable of randomly focusing light to provide a caustic or speckle pattern, as described herein. In some implementations, diffuser 260 may be positioned to receive light remitted from a patient's eye, and may provide caustic or speckle patterns based on the remitted light for purposes of obtaining aberrometry measurements and high-resolution images of anterior and posterior segments of the patient's eye, as described elsewhere herein.

User device 270 includes one or more devices capable of receiving, generating, storing, processing, and/or providing information associated with computational lightfield ophthalmoscope device 205. For example, user device 270 may include a communication and/or computing device, such as a mobile phone (e.g., a smart phone, a radiotelephone, etc.), a desktop computer, a laptop computer, a tablet computer, a handheld computer, a gaming device, a wearable communication device (e.g., a smart wristwatch, a pair of smart eyeglasses, etc.), or a similar type of device. In some implementations, user device 270 may receive image data from computational lightfield ophthalmoscope device 205 for analysis and processing, as described elsewhere herein.

Network 280 includes one or more wired and/or wireless networks. For example, network 280 can include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of components, devices, and networks shown in FIG. 2 are provided as an example. In practice, there can be additional components, devices, and/or networks, fewer components, devices, and/or networks, different components, devices, and/or networks, or differently arranged components, devices, and/or networks than those shown in FIG. 2. Furthermore, two or more components and/or devices shown in FIG. 2 can be implemented within a single component and/or device, or a single component or device shown in FIG. 2 can be implemented as multiple, distributed components and/or devices. Additionally, or alternatively, a set of components and/or devices (e.g., one or more components and/or devices) of environment 200 can perform one or more functions described as being performed by another set of components and/or devices of environment 200.

Figure 3:
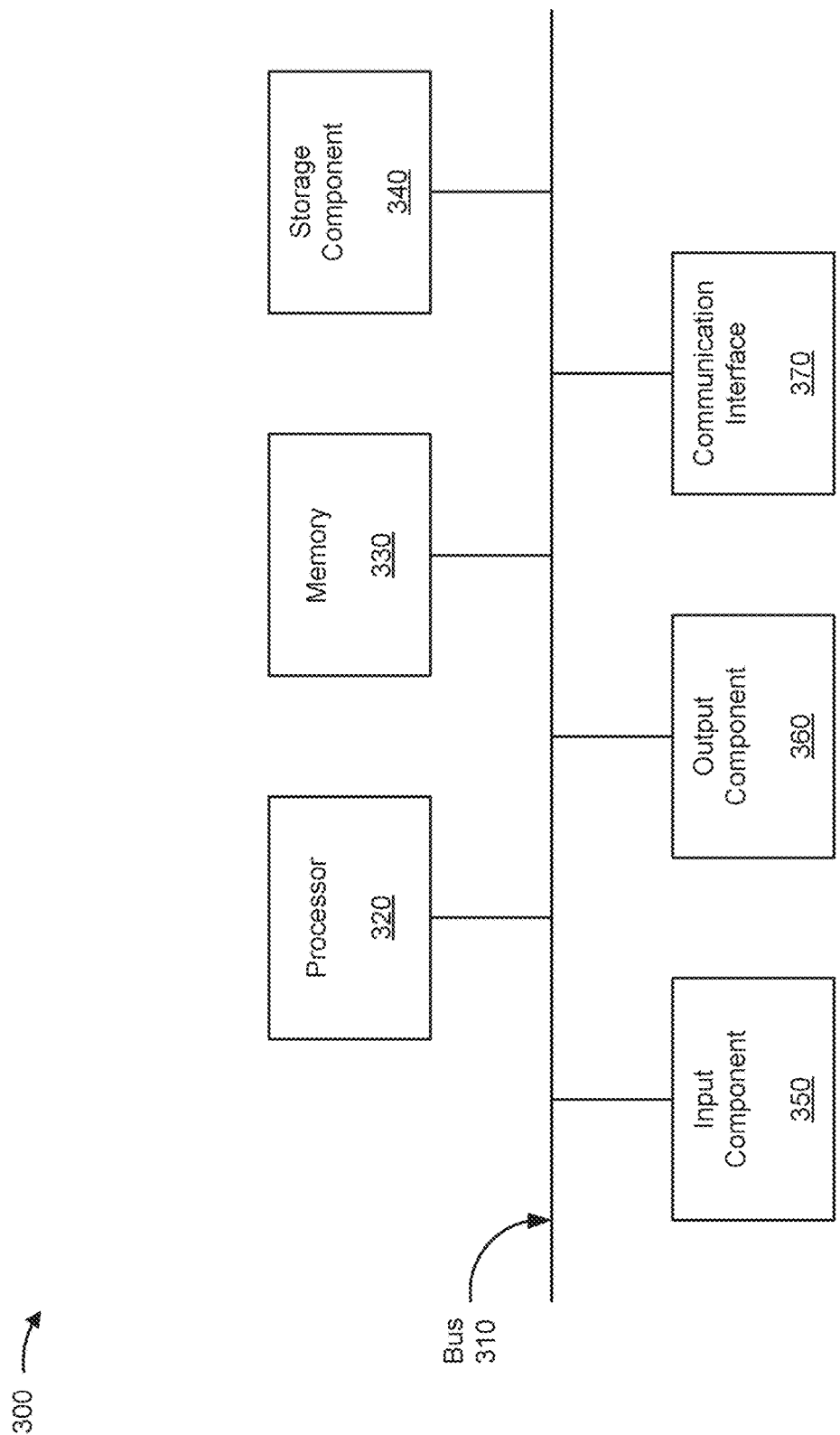
FIG. 3 is a diagram of example components of one or more devices of FIG. 2.

FIG. 3 is a diagram of example components of a device 300. Device 300 may correspond to computational lightfield ophthalmoscope device 205 and/or user device 270. In some implementations, computational lightfield ophthalmoscope device 205 and/or user device 270 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a GPU, an accelerated processing unit (APU), a microprocessor, a microcontroller, a digital signal processor (DSP), an FPGA, an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, an actuator, and/or image sensor(s) (e.g., camera(s))). Output component 360 includes a component that provides output information from device 300 (e.g., a display, a speaker, and/or one or more LEDs).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a wireless local area network interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
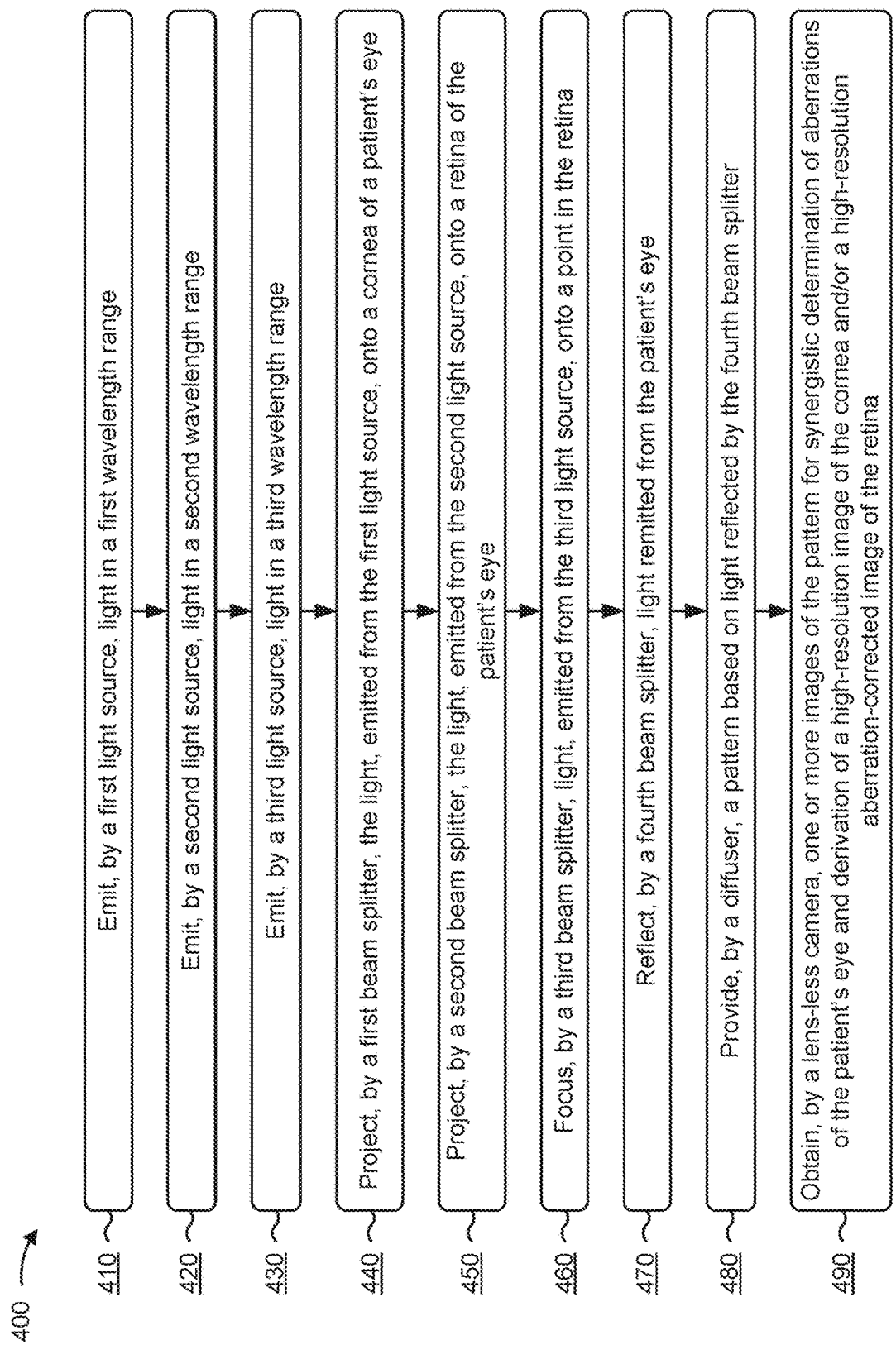
FIG. 4 is a flow chart of an example process for simultaneous, or near simultaneous, ocular imaging and aberrometry using a computational lightfield ophthalmoscope device.

FIG. 4 is a flow chart of an example process 400 for simultaneous, or near simultaneous, ocular imaging and aberrometry using a computational lightfield ophthalmoscope device. In some implementations, one or more process blocks of FIG. 4 may be performed by a computational lightfield ophthalmoscope device (e.g., computational lightfield ophthalmoscope device 205). In some implementations, one or more process blocks of FIG. 4 may be performed by another device or a group of devices separate from or including the computational lightfield ophthalmoscope device. In some implementations, the computational lightfield ophthalmoscope device may include a first light source (e.g., a first light source 240), a second light source (e.g., a second light source 240), a third light source (e.g., a third light source 240), and a fourth light source (e.g., a fourth light source 240). In some implementations, the computational lightfield ophthalmoscope device may include a first beam splitter, a second beam splitter, a third beam splitter, and a fourth beam splitter. In some implementations, the computational lightfield ophthalmoscope device may include a diffuser (e.g., diffuser 260) and a lens-less camera (e.g., an image sensor 250).

As shown in FIG. 4, process 400 may include emitting light in a first wavelength range (block 410). For example, the first light source may emit light in a first wavelength range, as described above in connection with FIGS. 1A-1L.

As further shown in FIG. 4, process 400 may include emitting light in a second wavelength range (block 420). For example, the second light source may emit light in a second wavelength range, as described above in connection with FIGS. 1A-1L.

As further shown in FIG. 4, process 400 may include emitting light in a third wavelength range (block 430). For example, the third light source may emit light in a third wavelength range, as described above in connection with FIGS. 1A-1L.

As further shown in FIG. 4, process 400 may include projecting the light, emitted from the first light source, onto a cornea of a patient's eye (block 440). For example, the first beam splitter may project the light, emitted from the first light source, onto a cornea of a patient's eye, as described above in connection with FIGS. 1A-1L.

As further shown in FIG. 4, process 400 may include projecting the light, emitted from the second light source, onto a retina of the patient's eye (block 450). For example, the second beam splitter may project the light, emitted from the second light source, onto a retina of the patient's eye, as described above in connection with FIGS. 1A-1L.

As further shown in FIG. 4, process 400 may include focusing light, emitted from the third light source, onto a point in the retina (block 460). For example, the third beam splitter may focus light, emitted from the third light source, onto a point in the retina, as described above in connection with FIGS. 1A-1L.

As further shown in FIG. 4, process 400 may include reflecting light remitted from the patient's eye (block 470). For example, the fourth beam splitter may reflect light remitted from the patient's eye, as described above in connection with FIGS. 1A-1L.

As further shown in FIG. 4, process 400 may include providing a pattern based on light reflected by the fourth beam splitter (block 480). For example, the diffuser may provide a pattern based on light reflected by the fourth beam splitter, as described above in connection with FIGS. 1A-1L.

As further shown in FIG. 4, process 400 may include obtaining one or more images of the pattern for synergistic determination of aberrations of the patient's eye and derivation of a high-resolution image of the cornea and/or a high-resolution aberration-corrected image of the retina (block 490). For example, the lens-less camera may obtain one or more images of the pattern for synergistic determination of aberrations of the patient's eye and derivation of a high-resolution image of the cornea and/or a high-resolution aberration-corrected image of the retina, as described above in connection with FIGS. 1A-1L.

Process 400 may include additional implementations, such as any single implementation or any combination of implementations described below and/or in connection with one or more other processes described elsewhere herein.

In some implementations, the diffuser may be composed of glass and/or plastic. In some implementations, process 400 may include obtaining a plurality of images of the pattern during natural, rapid movements of the patient's eye. In some implementations, the lens-less camera may include a plenoptic camera. In some implementations, the lens-less camera may be positioned, at a distance from the diffuser, in, or proximate to, a plane in which imaging of the pattern is at a sharpness that satisfies a threshold. In some implementations, the lens-less camera may include a red-green-blue (RGB) image sensor.

In some implementations, determination of the aberrations of the patient's eye and derivation of the high-resolution image of the cornea and/or the high-resolution aberration-corrected image of the retina is to be performed using a machine learning model. In some implementations, derivation of the high-resolution image of the cornea and/or the high-resolution aberration-corrected image of the retina is to be performed by digital refocusing of the one or more images or by processing the one or more images using a sharpness maximization algorithm. In some implementations, derivation of the high-resolution image of the cornea and/or the high-resolution aberration-corrected image of the retina is to be performed by digital refocusing of the one or more images, where the digital refocusing increases a sharpness of a plurality of regions associated with a field of view of the one or more images.

In some implementations, a device for ocular diagnostics may include one or more light sources configured to illuminate an anterior segment of a patient's eye, a diffuser positioned to receive light remitted from the anterior segment of the patient's eye, and configured to provide a pattern based on the light remitted, and an image sensor configured to obtain one or more images of the pattern to enable determination of one or more properties of the patient's eye.

In some implementations, the one or more properties may include refractive errors usable to calculate an eyeglass prescription needed for vision correction. In some implementations, the one or more images may enable derivation of an image of a fundus of the patient's eye. In some implementations, the one or more properties may include an aberration profile usable to calculate a precise measurement of an eyeglass prescription needed for vision correction. In some implementations, the aberration profile may enable reconstruction of a high-resolution image of a retina of the patient's eye.

In some implementations, a computational lightfield ophthalmoscope device may include a first light source configured to emit light in a first wavelength range, a second light source configured to emit light in a second wavelength range, a third light source configured to emit light in a third wavelength range, a first beam splitter arranged to project light, emitted from the first light source, onto an anterior segment of a patient's eye, a second beam splitter arranged to project light, emitted from the second light source, onto a posterior segment of the patient's eye, a third beam splitter arranged to focus light, emitted from the third light source, onto a point in the posterior segment of the patient's eye, a fourth beam splitter arranged to reflect light remitted from the patient's eye, a diffuser positioned to receive light reflected by the fourth beam splitter, and configured to provide a pattern based on the light reflected by the fourth beam splitter, and an image sensor configured to obtain one or more images of the pattern for simultaneous, or near simultaneous, determination of aberrations of the patient's eye and derivation of a high-resolution image of the anterior segment of the patient's eye and a high-resolution aberration-corrected image of the posterior segment of the patient's eye.

In some implementations, the computational lightfield ophthalmoscope device may include one or more memories, and one or more processors, communicatively coupled to the one or more memories, to process the one or more images to generate a first image of a first pattern associated with the light emitted from the first light source, a second image of a second pattern associated with the light emitted from the second light source, and a third image of a third pattern associated with the light emitted from the third light source. In some implementations, the determination of the aberrations and the derivation, of the high-resolution image of the anterior segment of the patient's eye and the high-resolution aberration-corrected image of the posterior segment of the patient's eye, may be based on the first image, the second image, and the third image.

In some implementations, the one or more processors may perform a non-rigid image registration process on the third image and a reference image to determine an eyeglass prescription for the patient's eye. In some implementations, the reference image may be derived, using the computational lightfield ophthalmoscope device, based on a planar wavefront. In some implementations, the one or more processors may process the third image using an artificial neural network to determine an eyeglass prescription for the patient's eye.

In some implementations, the one or more processors may cause the image sensor to obtain a plurality of images of the pattern, and process the plurality of images to derive a first set of images of at least a first pattern associated with the light emitted from the first light source, and a second set of images of at least a second pattern associated with the light emitted from the second light source. In some implementations, the one or more processors may perform an iterative image reconstruction process on the first set of images and on the second set of images to derive the high-resolution image of the anterior segment of the patient's eye and the high-resolution aberration-corrected image of the posterior segment of the patient's eye.

In some implementations, the one or more processors may cause the first light source, the second light source, and the third light source to simultaneously, or near simultaneously, emit the light in the first wavelength range, the light in the second wavelength range, and the light in the third wavelength range. In some implementations, the first wavelength range may correspond to a green color, the second wavelength range may correspond to a red color, and the third wavelength range may correspond to a blue color. In some implementations, the first light source is configured to emit light first in a sequence, the second light source is configured to emit light second in the sequence, the third light source is configured to emit light third in the sequence, and the image sensor is configured to obtain sequential images of the pattern based on the sequence. In some implementations, the computational lightfield ophthalmoscope device may be implemented in a mobile device.

In some implementations, a computational lightfield ophthalmoscope device may include a first light source configured to periodically emit light at a first frequency, a second light source configured to periodically emit light at a second frequency, a third light source configured to periodically emit light at a third frequency, a first beam splitter arranged to project light, emitted from the first light source, onto an anterior segment of a patient's eye, a second beam splitter arranged to project light, emitted from the second light source, onto a posterior segment of the patient's eye, a third beam splitter arranged to focus light, emitted from the third light source, onto a point in the posterior segment of the patient's eye, a fourth beam splitter arranged to reflect light remitted from the patient's eye, a diffuser positioned to receive light reflected by the fourth beam splitter, and configured to provide a pattern based on the light reflected by the fourth beam splitter, and a camera configured to obtain one or more plenoptic images based on the pattern for simultaneous, or near simultaneous, determination of aberrations of the patient's eye and derivation of high-resolution images of the anterior segment of the patient's eye and the posterior segment of the patient's eye.

In some implementations, one or more of the first light source, the second light source, or the third light source may include a light-emitting diode, a vertical-cavity surface-emitting laser (VCSEL), or a laser diode. In some implementations, the camera may include a complementary metal-oxide-semiconductor (CMOS) sensor.

In some implementations, the first light source, the second light source, and the third light source may each be configured to emit light in a particular wavelength range. In some implementations, the camera may include a monochrome sensor configured to detect light in the particular wavelength range. In some implementations, the diffuser may have a length that enables imaging, of the posterior segment of the patient's eye, at a numerical aperture that satisfies a threshold value.

In some implementations, the computational lightfield ophthalmoscope device may include a tunable lens positioned between the diffuser and the camera that permits adjustment of a conjugate imaging plane of the camera to different positions relative to the diffuser. In some implementations, the computational lightfield ophthalmoscope device may include an additional diffuser positioned proximate to one or more of the first light source, the second light source, or the third light source, for reducing laser speckles.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

In this way, all objective measurements of a comprehensive ocular exam may be provided using a single device or system. Employing a single computational lightfield ophthalmoscope device, such as that described herein, is advantageous over existing ocular examination instrumentation, since a single device can be used for refraction examination and imaging of anterior and posterior segments of a patient's eye. This reduces or eliminates a need to utilize three prior, complex systems (i.e., an autorefractor, a traditional ophthalmoscope, and a slit lamp) to conduct an eye exam, which simplifies, and reduces the costs of, such exams, thereby making affordable eye care accessible to more people. Additionally, a device that includes a minimal quantity of components—e.g., a light source (e.g., a light-emitting diode), a diffuser, and an image sensor, as described herein—and that provides objective measurements, reduces or eliminates a need for trained eye care providers to conduct eye exams, which also reduces the costs, and improves the overall accuracy, of such exams, thereby yielding more precise eyeglass prescriptions. Furthermore, utilizing a device, as described herein, provides synergistic measurements—e.g., wavefront information may be used to reconstruct higher quality retinal images, and such retinal images may be used to inform aberration measurements. This reduces or eliminates a need to utilize expensive closed-loop adaptive optics systems that may otherwise be needed to obtain high-resolution retinal images. High-resolution images of the fundus, provided by implementations described herein, also enable applications beyond eye examinations, including the assessment of various conditions relating to the brain (e.g., stroke severity, brain injury, neurodegenerative diseases, and/or the like), given that the retina may be a non-invasive portal to the brain. Such images of the fundus may also enable the assessment of a variety of health metrics, including, for example, blood pressure, cardiovascular risk factors, age, and/or the like.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, and/or the like.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "only one" or similar language is used. Also, as used herein, the terms "has," "have," "having," and/or the like are intended to be open-ended terms. Further, the phrase "based on" is intended to mean "based, at least in part, on" unless explicitly stated otherwise.

What is claimed is:

1. A device for ocular diagnostics, comprising:
    a first light source configured to illuminate an anterior segment of a patient's eye with a first range of illumination wavelengths;
    a second light source configured to illuminate an anterior segment of a patient's eye with a second range of illumination wavelengths, wherein the first range of wavelengths is different than the second range of wavelengths;
    a diffuser positioned to receive light remitted from the anterior segment of the patient's eye during ocular diagnosis based on the first range of wavelengths and the second range of wavelengths, and configured to provide a pattern based on the light remitted;
    an image sensor configured to obtain one or more images of the pattern provided by the diffuser; and
    a processor, in communication with the image sensor, and a computer readable medium that stores a trained machine learning model that is trained using a training dataset that comprises retinal images and associated diffuser patterns of the retinal images that are generated by a computational lightfield ophthalmoscope and when executed by the processor enables determination of one or more properties of the patient's eye,
    wherein the diffuser is arranged in front of a sensing side of the image sensor.

2. The device of claim 1, wherein the one or more properties include refractive errors usable to calculate an eyeglass prescription needed for vision correction.

3. The device of claim 1, wherein the one or more images enable derivation of an image of a fundus of the patient's eye.

4. The device of claim 1, wherein the one or more properties include an aberration profile usable to calculate a precise measurement of an eyeglass prescription needed for vision correction.

5. The device of claim 4, wherein the aberration profile enables reconstruction of a high-resolution image of a retina of the patient's eye.

6. The device of claim 1, wherein the image sensor includes a cellular phone camera.

7. A computational lightfield ophthalmoscope device, comprising:
a first light source configured to emit light in a first wavelength range; a second light source configured to emit light in a second wavelength range;
a third light source configured to emit light in a third wavelength range;
a first beam splitter arranged to project light, emitted from the first light source, onto an anterior segment of a patient's eye;
a second beam splitter arranged to project light, emitted from the second light source, onto a posterior segment of the patient's eye;
a third beam splitter arranged to focus light, emitted from the third light source, onto a point in the posterior segment of the patient's eye;
a fourth beam splitter arranged to reflect light remitted from the patient's eye;
a diffuser positioned to receive light reflected by the fourth beam splitter, and configured to provide a pattern based on the light reflected by the fourth beam splitter; and
an image sensor configured to obtain one or more images of the pattern for simultaneous, or near simultaneous, determination of aberrations of the patient's eye and derivation of a high-resolution image of the anterior segment of the patient's eye and a high-resolution aberration-corrected image of the posterior segment of the patient's eye.

8. The computational lightfield ophthalmoscope device of claim 7, further comprising:
one or more memories; and
one or more processors, communicatively coupled to the one or more memories, to:
process the one or more images to generate:
a first image of a first pattern associated with the light emitted from the first light source;
a second image of a second pattern associated with the light emitted from the second light source, and
a third image of a third pattern associated with the light emitted from the third light source;
wherein the determination of the aberrations and the derivation, of the high-resolution image of the anterior segment of the patient's eye and the high-resolution aberration-corrected image of the posterior segment of the patient's eye, are based on the first image, the second image, and the third image.

9. The computational lightfield ophthalmoscope device of claim 8, wherein the one or more processors are further to:
perform a non-rigid image registration process on the third image and a reference image to determine an eyeglass prescription for the patient's eye,
the reference image being derived, using the computational lightfield ophthalmoscope device, based on a planar wavefront.

10. The computational lightfield ophthalmoscope device of claim 8, wherein the one or more processors are further to:
process the third image using an artificial neural network to determine an eyeglass prescription for the patient's eye.

11. The computational lightfield ophthalmoscope device of claim 8, wherein the one or more processors are further to:
cause the image sensor to obtain a plurality of images of the pattern;
process the plurality of images to derive:
a first set of images of at least a first pattern associated with the light emitted from the first light source; and
a second set of images of at least a second pattern associated with the light emitted from the second light source; and
perform an iterative image reconstruction process on the first set of images and on the second set of images to derive the high-resolution image of the anterior segment of the patient's eye and the high-resolution aberration-corrected image of the posterior segment of the patient's eye.

12. The computational lightfield ophthalmoscope device of claim 8, wherein the one or more processors are further to:
cause the first light source, the second light source, and the third light source to simultaneously, or near simultaneously, emit the light in the first wavelength range, the light in the second wavelength range, and the light in the third wavelength range.

13. The computational lightfield ophthalmoscope device of claim 7, wherein the first wavelength range corresponds to a green color, the second wavelength range corresponds to a red color, and the third wavelength range corresponds to a blue color.

14. The computational lightfield ophthalmoscope device of claim 7,
wherein the first light source is configured to emit light first in a sequence, the second light source is configured to emit light second in the sequence, and the third light source is configured to emit light third in the sequence, wherein the image sensor is configured to obtain sequential images of the pattern based on the sequence.

15. The computational lightfield ophthalmoscope device of claim 7, wherein the computational lightfield ophthalmoscope device is implemented in a mobile device.

16. A computational lightfield ophthalmoscope device, comprising:
a first light source configured to periodically emit light at a first frequency;
a second light source configured to periodically emit light at a second frequency;
a third light source configured to periodically emit light at a third frequency;
a first beam splitter arranged to project light, emitted from the first light source, onto an anterior segment of a patient's eye;
a second beam splitter arranged to project light, emitted from the second light source, onto a posterior segment of the patient's eye;
a third beam splitter arranged to focus light, emitted from the third light source, onto a point in the posterior segment of the patient's eye;
a fourth beam splitter arranged to reflect light remitted from the patient's eye;
a diffuser positioned to receive light reflected by the fourth beam splitter, and configured to provide a pattern based on the light reflected by the fourth beam splitter; and
a camera configured to obtain one or more plenoptic images based on the pattern for simultaneous, or near simultaneous, determination of aberrations of the patient's eye and derivation of high-resolution images of the anterior segment of the patient's eye and the posterior segment of the patient's eye.

17. The computational lightfield ophthalmoscope device of claim 16, wherein one or more of the first light source, the second light source, or the third light source include:
   a light-emitting diode,
   a vertical-cavity surface-emitting laser (VCSEL), or
   a laser diode.

18. The computational lightfield ophthalmoscope device of claim 16, wherein the camera includes a complementary metal-oxide-semiconductor (CMOS) sensor.

19. The computational lightfield ophthalmoscope device of claim 16, wherein the first light source, the second light source; and the third light source are each configured to emit light in a particular wavelength range; and
   wherein the camera includes a monochrome sensor configured to detect light in the particular wavelength range.

20. The computational lightfield ophthalmoscope device of claim 16, wherein the diffuser has a length that enables imaging, of the posterior segment of the patient's eye, at a numerical aperture that satisfies a threshold value.

21. The computational lightfield ophthalmoscope device of claim 16, further comprising:
   a tunable lens positioned between the diffuser and the camera that permits adjustment of a conjugate imaging plane of the camera to different positions relative to the diffuser.

22. The computational lightfield ophthalmoscope device of claim 16, further comprising:
   an additional diffuser, positioned proximate to one or more of the first light source, the second light source, or the third light source, for reducing laser speckles.

23. A method, comprising:
   emitting, by a first light source of a lightfield ophthalmoscope device, light in a first wavelength range;
   emitting, by a second light source of the lightfield ophthalmoscope device, light in a second wavelength range;
   emitting, by a third light source of the lightfield ophthalmoscope device, light in a third wavelength range;
   projecting, by a first beam splitter of the lightfield ophthalmoscope device, the light, emitted from the first light source, onto a cornea of a patient's eye;
   projecting, by a second beam splitter of the lightfield ophthalmoscope device, the light, emitted from the second light source, onto a retina of the patient's eye;
   focusing, by a third beam splitter of the lightfield ophthalmoscope device, light, emitted from the third light source, onto a point in the retina;
   reflecting, by a fourth beam splitter of the lightfield ophthalmoscope device, light remitted from the patient's eye;
   providing, by a diffuser of the lightfield ophthalmoscope device, a pattern based on light reflected by the fourth beam splitter; and
   obtaining, by a lens-less camera of the lightfield ophthalmoscope device, one or more images of the pattern for synergistic determination of aberrations of the patient's eye and derivation of a high-resolution image of the cornea and/or high-resolution aberration-corrected image of the retina.

24. The method of claim 23, wherein the diffuser is composed of glass and/or plastic.

25. The method of claim 23, wherein obtaining the one or more images comprises:
   obtaining a plurality of images of the pattern during natural, rapid movements of the patient's eye.

26. The method of claim 23, wherein the lens-less camera includes a plenoptic camera.

27. The method of claim 23, wherein the lens-less camera is positioned, at a distance from the diffuser, in, or proximate to, a plane in which imaging of the pattern is at a sharpness that satisfies a threshold.

28. The method of claim 23, wherein the lens-less camera includes a red-green-blue (RGB) image sensor.

29. The method of claim 23, wherein determination of the aberrations of the patient's eye and derivation of the high-resolution image of the cornea and/or the high-resolution aberration-corrected image of the retina is to be performed using a machine learning model.

30. The method of claim 23, wherein derivation of the high-resolution image of the cornea and/or the high-resolution aberration-corrected image of the retina is to be performed by digital refocusing of the one or more images or by processing the one or more images using a sharpness maximization algorithm.

31. The method of claim 23, wherein derivation of the high-resolution image of the cornea and/or the high-resolution aberration-corrected image of the retina is to be performed by digital refocusing of the one or more images,
   wherein the digital refocusing increases a sharpness of a plurality of regions associated with a field of view of the one or more images.

\* \* \* \* \*

UNITED STATES PATENT AND TRADEMARK OFFICE
CERTIFICATE OF CORRECTION

PATENT NO. : 12,376,744 B2  
APPLICATION NO. : 16/972483  
DATED : August 5, 2025  
INVENTOR(S) : Nicholas J. Durr et al.

Page 1 of 1

It is certified that error appears in the above-identified patent and that said Letters Patent is hereby corrected as shown below:

On the Title Page

Item (72) Under Inventors, the last name of the last listed inventor should be:
--McKay-- instead of "Mckay"

Signed and Sealed this  
Fourth Day of November, 2025

John A. Squires  
*Director of the United States Patent and Trademark Office*